United States Patent
Ueno et al.

[11] Patent Number: 5,889,196
[45] Date of Patent: Mar. 30, 1999

[54] GAS COMPOSITION SENSOR AND METHOD FOR SEPARATELY DETECTING COMPONENTS OF EXHAUST GAS TO DIAGNOSE CATALYTIC CONVERTER PERFORMANCE

[75] Inventors: Sadayasu Ueno; Shirou Ouchi; Naoki Minami, all of Hitachinaka, Japan

[73] Assignees: Hitachi, Ltd.; Hitachi Car Engineering Co., Ltd., both of Japan

[21] Appl. No.: 778,763

[22] Filed: Jan. 6, 1997

[30] Foreign Application Priority Data

Jan. 5, 1996 [JP] Japan .................................. 8-000341

[51] Int. Cl.$^6$ .................................................. G01N 27/407
[52] U.S. Cl. ........................ 73/23.31; 73/31.06; 204/429
[58] Field of Search ................... 73/23.31, 23.32, 73/31.05, 31.06; 204/424, 427, 428, 429, 425

[56] References Cited

U.S. PATENT DOCUMENTS

| | | | |
|---|---|---|---|
| 4,105,524 | 8/1978 | Fujishiro et al. | 204/427 X |
| 4,145,272 | 3/1979 | Nakamura et al. | 204/428 X |
| 4,383,906 | 5/1983 | Sano et al. | 204/424 X |
| 4,629,535 | 12/1986 | Oyama et al. | 204/425 X |
| 4,803,866 | 2/1989 | Miki et al. | 73/23.32 |
| 4,828,673 | 5/1989 | Maeda | 204/424 |
| 4,935,118 | 6/1990 | Agarwal et al. | 204/424 X |
| 5,268,086 | 12/1993 | Hamburg et al. | 204/424 X |

FOREIGN PATENT DOCUMENTS

| | | |
|---|---|---|
| 1-101455 | 4/1989 | Japan . |
| 2-30915 | 2/1990 | Japan . |
| 2-33408 | 2/1990 | Japan . |
| 2-207159 | 8/1990 | Japan . |
| 3-74540 | 3/1991 | Japan . |
| 3-293544 | 12/1991 | Japan . |
| 4-17141 | 1/1992 | Japan . |
| 4-109021 | 4/1992 | Japan . |
| 7-34860 | 2/1995 | Japan . |

*Primary Examiner*—Michael Brock
*Attorney, Agent, or Firm*—Evenson, McKeown, Edwards & Lenahan, P.L.L.C.

[57] ABSTRACT

A gas composition sensor for detecting oxygen, and hydrocarbon group fuel or combustible composition produced after combustion having a zirconia solid electrolyte body, a concentration cell composed of a platinoid metal catalytic detecting electrode and a reference electrode opposite to each other and a sensing element composed of a gas diffusion limiting member coating the detecting electrode, which further comprises a pair of the sensing elements and heaters for setting both of the sensing elements to operating temperatures different from each other, whereby a specified gas component is selectively detected by operating both of the sensing elements so as to have sensitivity coefficients to the specified gas component different from each other.

16 Claims, 13 Drawing Sheets

FIG. 7
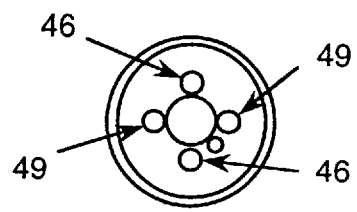
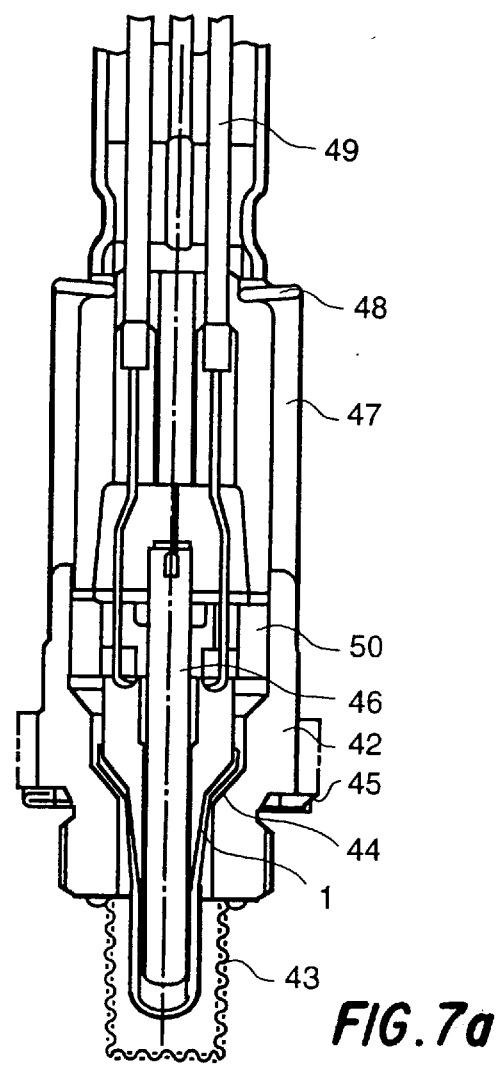
FIG. 7a

GAS COMPOSITION SENSOR AND METHOD FOR SEPARATELY DETECTING COMPONENTS OF EXHAUST GAS TO DIAGNOSE CATALYTIC CONVERTER PERFORMANCE

BACKGROUND OF THE INVENTION

The present invention relates to a gas component sensor for detecting oxygen, hydrocarbon fuel, combustible composition after combustion of the fuel and so on, and a diagnosis system and a control system using the gas composition sensor, and a diagnosis method and a control method using the gas composition sensor, and more particularly to a gas composition sensor used for diagnosing exhaust gas purifying performance of a catalytic converter for a vehicle engine, for detecting an air-to-fuel ratio of a general combustion machine and for detecting or alarming fuel gas leakage of municipal gas.

In general, in the field of air-to-fuel ratio control for an engine, there are a system in which an air-to-fuel ratio is controlled to be stabilized to a stoichiometric air-to-fuel ratio by combining a three way catalyst and an oxygen sensor, and a system in which an air-to-fuel ratio is controlled so that lean-burn is effected within a zone between the stoichiometric air-to-fuel ratio and a lean limit boundary using an air-to-fuel sensor. Further, it will become compulsory to install a hydrocarbon sensor on an engine mounted on a vehicle in order to diagnosing the catalyst by the on-board sensor, and it will become indispensable in connection with an exhaust gas regulation to develop a technology of controlling an air-to-fuel ratio in an air intake system of an engine by detecting an exhaust-gas-recirculation gas or a purged fuel vapor in the air intake system.

In the past, diagnosis systems of exhaust gas purifying catalyst for an engine were disclosed, for example, in Japanese Patent Application Laid-Open No. 7-34860, Japanese Patent Application Laid-Open No. 3-293544, Japanese Patent Application Laid-Open No. 4-109021, Japanese Patent Application Laid-Open No. 1-101455, Japanese Patent Application Laid-Open No. 4-17141, Japanese Patent Application Laid-Open No. 3-74540, Japanese Patent Application Laid-Open No. 2-207159, Japanese Patent Application Laid-Open No. 2-33408 and Japanese Patent Application Laid-Open No. 2-30915. In the diagnosis systems, oxygen sensors or air-to-fuel ratio sensors are arranged in both upstream and downstream sides of a catalyst converter provided in an exhaust pipe, and purifying performance for combustibles and so on of the catalyst converter is derived from an inter-correlation of transient wave-forms or a concentration ratio of the detected signals in regard to oxygen or combustibles detected by the sensors.

Instead of the oxygen sensor or the combustible gas sensor described above, it is also proposed to employ a sensor for a specified detecting object such as $NO_x$, HC, CO or the like. However, the proposal does not propose any practical structure nor any practical material for the sensors, but discloses only a proposal in regard to algorithm for diagnosing a catalyst converter. Even the sensor for a specified detecting object needs to be further improved in its performance and in its durability for practical use.

Other than the sensors described above, there are few kinds of proven gas composition sensors which can accurately measure an amount of combustible composition, remaining oxygen and the like in the combustion gas of an engine under a highly corrosive, soiled and high temperature environment. However, one of the few proven gas composition sensors capable of being used under such an environment is a so-called air-to-fuel ratio sensor which is a gas composition sensor formed by combining a zirconia concentration cell and a member limiting gas diffusion.

Mechanism of gas detecting of the air-to-fuel ratio sensor is that amounts of oxygen and combustibles such as HC, CO, $H_2$ are linearly measured as oxygen ion currents in positive and negative directions respectively by means of oxidizing reaction and gas ion exchange reaction of catalytic function of platinoid metal electrodes. In order to maintain a required measuring accuracy of the air-to-fuel ratio sensor for a long time period, it is necessary to suppress degradation of the catalytic function due to soiling and corrosion of the electrodes, to maintain temperature of the pair of cells stable and to calibrate the output characteristic using a gas having a known concentration such as atmospheric air.

According to a recent research result on diagnosis of degradation of a catalytic converter for an engine mounted on a vehicle, in the conventional diagnosing method in which oxygen sensors are arranged in the upstream side and the downstream side of the catalytic converter and signal waveforms from the oxygen sensors are compared, an amount of all the combustibles such as CO, HC and the like are measured together and a degradation level of the catalytic converter is diagnosed by the purifying function for the total amount of the combustibles. As a result, the degradation level of the catalytic converter is estimated only by the purifying function of CO which is a dominant component of the combustible gas composition. Therefore, it is revealed and becomes a trouble that there are many cases where the catalytic converter is diagnosed as degraded even though the purifying function for HC of main object to be diagnosed is not degraded so low that the catalyst should be exchanged. The conventional HC sensor and the conventional CO sensor cannot cope with the above problem since they are not proven in exhaust gas measurement at the present state.

On the other hand, although it is a proven technology to measure the total amount of oxygen and the combustible gas composition together using the oxygen sensor and the air-to-fuel ratio sensor, it has not proposed to separately measure each amount of components, HC or CO, for the purpose of diagnosing a catalytic converter. Therefore, there is a problem in diagnosis of purifying performance for HC or CO.

Further, similarly to the case of diagnosis of catalytic converter, neither the HC sensor nor the CO sensor can cope with exhaust gas measurement in the present state since it has not been practically used. Although the oxygen sensor and the air-to-fuel ratio sensor have been practically used in measuring a total amount of oxygen and combustibles in a exhaust gas, it has not been disclosed to separately measure a concentration of HC or CO having different molecular weight.

Furthermore, when vapor fuel from a fuel tank is purged in an intake system of a gasoline engine, an amount of fuel injected from an injection nozzle is controlled so as to be corrected by measuring an amount of the vapor fuel. In a diesel engine, in order to optimize trade-off relationship between $NO_x$ and PM (particulate matter), it is required to measure an amount of exhaust gas recirculated to intake air, that is, an exhaust gas recirculation ratio to perform critical control of the exhaust gas recirculation ratio. In order to cope with the control, it is required to measure the concentration of the vapor fuel in the intake air and the amount of the combustible composition in the exhaust gas separately.

However, there is not proposed any sensor capable of sufficiently coping with such measurement.

On the other hand, as for hydrocarbon group gas such as municipal gas used as a fuel for a common combustion apparatus other than the engine, an $SnO_2$ sensor or the like is practically used as a detecting device for detecting leakage of the gas. However, the sensor is not sufficient in selectiveness for application to the specified gas and in stability of sensing sensitivity which should be improved.

It is required for the alarming device of fuel gas leakage that various kinds of combustible compositions of hydrocarbons having comparatively small molecular weights in the fuel gas can be detected at a high sensitivity by separating from mono-oxide carbon by the sensor, the other hydrocarbons of non-fuel group having comparatively large molecular weights can be automatically discriminated, and the leakage can be judged to be continuous but not transient. These characteristics are also problems in the conventional sensor to be improved. Further, it is required for the device for alarming incomplete combustion in the gas combustion apparatus that noxious CO component in the gas combustion apparatus can be detected at a high sensitivity to alarm, and safety measures such as air ventilation can be performed if necessary. Thereby, it is required to develop a highly sensitive detecting sensor.

SUMMARY OF THE INVENTION

The present invention is made to solve the aforementioned problems. The object of the present invention is to provide a gas composition sensor capable of separately detecting each of gas components such as oxygen, and hydrocarbon group fuel or combustible gas and burned gas after combustion; and various kinds of diagnosis systems and control systems using the gas composition sensor; and methods for diagnosing and controlling using the gas composition sensor.

As for more detailed objects, a first object of the present invention is to diagnose purifying performance of a catalytic converter by accurately measure concentrations of oxygen and HC in an engine exhaust gas separately from the other combustible components, and to provide a gas composition sensor which can separately measure hydrocarbon group fuel gas and oxygen mixed in an intake air of the engine and further each of combustible components such as CO, HC and the like produced after combustion of the mixed gas and residual oxygen remaining after the combustion.

A second object of the present invention is to provide a gas composition sensor of which essential operation principle for selectively detecting HC is the principle of the conventional air-to-fuel sensor and which can withstand against a high temperature condition such as a condition in an engine.

A third object of the present invention is to provide a diagnosis system and a control system, and a diagnosing method and a control method which employ a gas composition sensor capable of maintaining a required diagnosis accuracy by adding a calibration function for time-dependent change in an output function and an initial variation of the gas composition sensor and compatible with environment resistivity, reliability and cost.

In order to attain the object described above, a gas composition sensor in accordance with the present invention is for detecting oxygen and hydrocarbon group fuel or combustible composition produced after combustion, and comprises a zirconia solid electrolyte body, a concentration cell composed of a platinoid metal catalytic detecting electrode and a reference electrode opposite to each other and a sensing element composed of a gas diffusion limiting member coating the detecting electrode, which further comprises a pair of the sensing elements and heaters for setting both of the sensing elements to operating temperatures different from each other. Thereby, a specified gas component is selectively detected by operating both of the sensing elements so as to have sensitivity coefficients to the specified gas component different from each other.

More detailed embodiments of the gas composition sensors in accordance with the present invention are characterized by that the pair of sensing elements are arranged on a common substrate, and share the solid electrolyte body, the reference electrode or the heater in case of necessity; one heater for heating the pair of sensing elements has an electric insulator member in the side of the sensing element and a heat insulating member in the side of detected gas and reference gas flow passages, and the heater is shared with the sensing elements to be heated; the pair of sensing elements share the solid electrolyte body, and share the reference electrode or the diffusion limiting member in case of necessity; and the pair of sensing elements share the diffusion limiting member, and share the solid electrolyte body, the reference electrode or the heater in case of necessity.

Further, the gas composition sensors in accordance with the present invention are characterized by that the pair of sensing elements are constructed in such that an operating temperature Tl of the sensing element in a low temperature side is not higher than 450° C. and the difference between an operating temperature Th of the sensing element in a high temperature side and the operating temperature Tl is not lower than 100° C.; the pair of gas composition sensing elements are sequentially controlled using a microcomputer; temperature of the sensing element in the low temperature side of the pair of sensing elements is controlled so as to be stabilized within a predetermined time period after starting of operation, and the sensing element in the high temperature side is positioned so that temperature of the sensing element in the high temperature side is controlled to a target temperature as the sensing element in the low temperature side is controlled, thereby hydrocarbon is selectively detected; and a reference air is introduced into the surrounding of the sensing element, a characteristic changing rate in an output function of the gas composition sensor is calibrated by comparing an output value under an oxygen concentration of the introduced reference air with a stored initial output value.

In a method of detecting a gas composition using the gas composition sensor described above in accordance with the present invention, when oxygen ion current signals Iph, Ipl of a gas composition detected by a pair of sensing elements set at temperatures Th, Tl different to each other are expressed by the following simultaneous equations (1), (2) having a concentration $X_{HC}$ of hydrocarbon group component and a concentration $Y_{CO}$ of the other component such as mono-oxide carbon as variables using four sensitivity coefficients $B_{hHC}$, $B_{hCO}$, $B_{1HC}$, $B_{1CO}$ which separate a gas composition into hydrocarbon group component and the other components such as mono-oxide carbon and are determined in advance using reference gases under the different temperatures of the pair of sensing elements, the simultaneous equations are solved and the concentrations $X_{HC}$ and $Y_{CO}$ are obtained from the following equations (3) and (4).

$$Iph = B_{hHC} X_{HC} + B_{hCO} Y_{CO} \quad (1)$$

$$Ipl = B_{1HC} X_{HC} + B_{1CO} Y_{CO} \quad (2)$$

$$X_{HC} = \{B_{1CO}Iph - B_{hCO}Ipl\} / \{B_{1CO}B_{hHC} - B_{hCO}B_{1HC}\} \quad (3)$$

$$Y_{CO} = \{B_{1HC}Iph - B_{hHC}Ipl\} / \{B_{1HC}B_{hCO} - B_{hHC}B_{1CO}\} \quad (4)$$

Further, a catalyst diagnosis system in accordance with the present invention comprises the gas composition sensor described above installed in the downstream side of a catalytic converter for purifying exhaust gas of an engine or the gas composition sensors installed between an exhaust gas manifold of an engine and a catalyst converter and between the downstream side of the catalyst converter and a muffler one for each, a means for selectively measuring a concentration of hydrocarbon component in the exhaust gas in the downstream side of the catalytic converter using the above gas composition sensor at a pre-determined time after every starting of engine operation when it is judged that the engine has been warmed up under a predetermined condition in connection with a regulated test mode on engine bench, and a means for calculating a purifying ability of the catalytic converter by executing a series of statistical processing such as averaging and comparison of the measured value using pre-stored data.

Furthermore, an engine control system using the gas composition sensor in accordance with the present invention is characterized by that the engine control system comprises a means for selectively detecting hydrocarbon using a pair of sensing elements during warming-up after starting of engine operation and for performing operating correction control such as fuel supply control or ignition timing control by detecting an air-to-fuel ratio using the sensing element in the high temperature side; that the engine control system controls in such a manner that when a fuel supply system is shut off to stop the engine, an ignition system and the other related systems are shut off after burning fuel having been supplied to the engine; that the engine control system comprises the gas composition sensors in a position near an intake manifold assembly of the engine intake air system where exhaust gas recirculation gas and purged vapor fuel are merged, and a means for correcting an amount of fuel supply based on an air-to-fuel ratio signal obtained from a detected signal of a high temperature sensing element of the gas composition sensor; and that the engine control system comprises the gas composition sensors described in any one of the item 1 to the item 13 in a position near an intake manifold assembly of the engine intake air system where exhaust gas recirculation gas and purged vapor fuel are merged, and a means for controlling an exhaust gas recirculation rate by calculating the exhaust gas recirculation rate from concentrations of mono-oxide carbon and hydrocarbon selectively obtained from the sensing element in the high temperature side and the sensing element in the low temperature side.

Further, a fuel gas leakage detecting system in accordance with the present invention is characterized by that the gas composition sensors described above is used as a detecting means for detecting fuel gas leakage or a detecting means for detecting incomplete combustion of fuel gas such as municipal gas, liquified petroleum gas, compressed natural gas or the like to operate an alarm, a safety valve and so on.

Description will be made below on a operating state where a gas composition sensor in accordance with the present invention constructed as described above is installed, for example, in an exhaust system of an engine.

When oxygen and combustible gas such as hydrocarbon and mono-oxide carbon are exist in an exhaust side of the engine, the combustible gas diffuses around two detecting electrodes of a concentration cell of the gas composition sensor which are stabilized at a temperature high enough to perform oxidation reaction, and the hydrocarbon and the mono-oxide carbon respectively react with the oxygen by catalytic action of the platinum electrode. When the remaining oxygen in the exhaust gas is consumed, oxygen is further transferred from the atmosphere in a form of ion current in order to maintain the electromotive force constant. The amount of current is an equivalent amount of surplus combustible composition of sum of the hydrocarbon and the mono-oxide carbon which is not oxidized by the oxygen in the exhaust side. In other words, the oxygen in the exhaust side and the combustible gas of the hydrocarbon and the mono-oxide carbon firstly react with each other inside the gas composition sensor, and an amount of the surplus combustible composition is measured as the oxygen current if the surplus combustible composition exists. However, the hydrocarbon and the mono-oxide carbon are not separately measured.

The present invention takes advantage of a characteristic that each of compositions such as mono-oxide carbon, hydrocarbon and so on composing a combustible gas has an intrinsic oxidizing reaction temperature, and each concentration of the gas components is obtained by solving simultaneous equations with two unknowns using two total oxygen ion current values measured by two detecting electrodes having different temperatures, that is, two sensing elements each of which has one or the other of the two electrodes in different temperatures to each other.

Concentrations of hydrocarbon and mono-oxide carbon can be separately measured by taking advantage of difference in relationships between temperature of the detecting electrode in the concentration cell and the detecting sensitivity for hydrocarbon and mono-oxide carbon, that is, difference in temperature dependence of gas detecting sensitivity for hydrocarbon and mono-oxide carbon. It is necessary to measure the sensitivity using an actual exhaust gas at actual temperature of the sensing element since molecular weight of hydrocarbon after combustion is small. Further, since the difference in gas detecting sensitivities for hydrocarbon and mono-oxide carbon is required to be large to a certain degree, it is preferable in taking various kinds of combustion into consideration that the temperature of the detecting electrode in the low temperature side is not higher than 450° C. and the temperature difference between the two detecting electrodes in the high temperature side and in the low temperature side is not smaller than 100° C.

In the catalyst diagnosis system for an engine or the engine control system using the gas composition sensor in accordance with the present invention, the gas composition sensor comprises a plug containing two sensing elements each of which has one or the other of a pair of detecting electrodes having different temperatures to each other, the gas composition sensor being installed at a position downstream of a catalytic converter, the engine being operated so as to correspond to a regulated test mode operating condition, concentration of hydrocarbon being calculated using the signals from the gas composition sensor to diagnose degradation of the catalyst.

During a period for approximately 60 seconds after just starting of an engine with throttle valve fully closed starting, for example, such as start idling operation with throttle valve fully closed, a volume of hydrocarbon and mono-oxide carbon in nearly the same order of the total displacement volume of the engine is exhausted. A concentration of hydrocarbon is measured by the gas composition sensor described above in the initial period of starting the engine because a concentration of hydrocarbon after completion of warming-up becomes too low to be detected. Therefore, a precondition for satisfying the present invention is purifying capability of the catalyst during the initial period of starting the engine when temperature of the catalyst is low.

Further, in order to perform measurement of exhaust gas after being purified using the gas composition sensor installed in the downstream of the catalytic converter, temperature condition at the time when the engine is started into operation must be within a pre-determined range, for example, the engine and the catalyst must be sufficiently cooled. Measurable exhaust gas temperature at starting the engine must be lower than the setting temperature of the sensing element in the low temperature side, and at that time both of the two detecting electrodes must be started so as to meet the time period for measuring.

The present invention described above can be summarized as follows.

1. A gas composition sensor for detecting oxygen, and hydrocarbon group fuel or combustible composition produced after combustion having a zirconia solid electrolyte body, a concentration cell composed of a detecting elect catalytic detecting electrode and a reference electrode opposite to each other and a sensing element composed of a gas diffusion limiting member coating the detecting electrode, which further comprises a pair of the sensing elements and heaters for setting both of the sensing elements to operating temperatures different from each other, whereby a specified gas component is selectively detected by operating both of the sensing elements so as to have sensitivity coefficients to the specified gas component different from each other.

2. The gas composition sensor described in the above item 1, wherein the pair of sensing elements are arranged on a common substrate, and share the solid electrolyte body, the reference electrode or the heater in case of necessity.

3. The gas composition sensor described in the above item 1, wherein one heater for heating the pair of sensing elements has an electric insulator member in the side of the sensing element and a heat insulating member in the side of detected gas and reference gas flow passages, and the heater is shared with the sensing elements to be heated.

4. The gas composition sensor described in the above item 1, wherein the pair of sensing elements share the solid electrolyte body, and share the reference electrode or the diffusion limiting member in case of necessity.

5. The gas composition sensor described in the above item 1, wherein the pair of sensing elements share the diffusion limiting member, and share the solid electrolyte body, the reference electrode or the heater in case of necessity.

6. The gas composition sensor described in the above item 1, wherein the pair of sensing elements are constructed in such that an operating temperature Tl of the sensing element in a low temperature side is not higher than 450° C. and the difference between an operating temperature Th of the sensing element in a high temperature side and the operating temperature Tl is not lower than 100° C.

7. The gas composition sensor described in the above item 1, which further comprises a controller for sequentially controlling the pair of gas composition sensing elements using a micro-computer.

8. The gas composition sensor described in the above item 7, wherein temperature of the sensing element in the low temperature side of the pair of sensing elements is controlled so as to be stabilized within a predetermined time period after starting of operation, the sensing element in the high temperature side is positioned so that temperature thereof is controlled to a target temperature as the sensing element in the low temperature side is controlled, thereby hydrocarbon is selectively detected.

9. The gas composition sensor described in the above item 7, wherein when a reference air is introduced into the surrounding of the sensing element, a characteristic changing rate in an output function of the gas composition sensor is calibrated by comparing an output value under an oxygen concentration of the introduced reference air with a stored initial output value.

10. A gas composition sensor for detecting oxygen, and hydrocarbon group fuel or combustible composition produced after combustion having a zirconia solid electrolyte body, a concentration cell composed of a platinoid metal catalytic detecting electrode and a reference electrode opposite to each other and a sensing element composed of a gas diffusion limiting member coating the detecting electrode, wherein the detecting electrode is arranged so as to be exposed to the oxygen, and the hydrocarbon group fuel or the combustible composition produced after combustion to be detected, and the reference electrode is exposed to atmospheric air or an atmosphere containing oxygen, and the gas composition sensor further comprises a single heater for heating the pair of sensing elements, the heater being coated with a ceramic layer to be heat-insulated and arranged so as to heat the pair of sensing elements to different temperatures.

11. A gas composition sensor for detecting oxygen, and hydrocarbon group fuel or combustible composition produced after combustion having a zirconia solid electrolyte body, a concentration cell composed of a platinoid metal catalytic detecting electrode and a reference electrode opposite to each other and a sensing element composed of a gas diffusion limiting member coating the detecting electrode, wherein the detecting electrode is arranged so as to be exposed to the oxygen, and the hydrocarbon group fuel or the combustible composition produced after combustion to be detected, and the reference electrode is exposed to atmospheric air or an atmosphere containing oxygen, and the gas composition sensor further comprises a single heater for heating the pair of sensing elements, a ceramic layer being provided between the heater and the sensing element to insulate between the sensing element and the heater and to moderate strain due to thermal expansion difference, a ceramic heat insulating coating layer being provided in the heater in the side opposite to the sensing element in case of necessity.

12. A gas composition sensor for detecting oxygen, and hydrocarbon group fuel and combustible composition produced after combustion having a zirconia solid electrolyte body, a concentration cell composed of a platinoid metal catalytic detecting electrode and a reference electrode opposite to each other and a sensing element composed of a gas diffusion limiting member coating the detecting electrode, wherein the pair of sensing elements are formed in a test-tube-shape, the detecting electrodes are arranged outside the solid electrolyte body in a shape of a pair of cylinders and the reference electrode is arranged over the whole inside surface of the solid electrolyte body to form a pair of concentration cells, the test-tube-shaped outside surface is coated with a gas diffusion limiting member made of a porous ceramic layer.

13. The gas composition sensor described in the above item 11, wherein the detecting electrode is arranged so as to be exposed to the oxygen, and the hydrocarbon group fuel or the combustible composition produced after combustion to be detected, and the reference electrode is exposed to atmospheric air or an atmosphere containing oxygen, and the gas composition sensor further comprises a single heater for heating the pair of sensing elements, the heater being mounted on a porous ceramic layer near a portion of the detecting electrode, a porous ceramic heat insulating coating layer being provided in the heater in the side opposite to the detecting electrode in case of necessity.

14. A method of detecting a gas composition using the gas composition sensor described in any one of the item 1 to the item 13, wherein when oxygen ion current signals Iph, Ipl of a gas composition detected by a pair of sensing elements set at temperatures Th, Tl different to each other are expressed by the following simultaneous equations (1), (2) having a concentration $X_{HC}$ of hydrocarbon group component and a concentration $Y_{CO}$ of the other component such as mono-oxide carbon as variables using four sensitivity coefficients $B_{hHC}$, $B_{hCO}$, $B_{1HC}$, $B_{1CO}$ which separate a gas composition into hydrocarbon group component and the other components such as mono-oxide carbon and are determined in advance using reference gases under the different temperatures of the pair of sensing elements, the simultaneous equations are solved and the concentrations $X_{HC}$ and $Y_{CO}$ are obtained from the following equations (3) and (4).

$$Iph = B_{hHC} X_{HC} + B_{hCO} Y_{CO} \quad (1)$$

$$Ipl = B_{1HC} X_{HC} + B_{1CO} Y_{CO} \quad (2)$$

$$X_{HC} = \{B_{1CO} Iph - B_{hCO} Ipl\} / \{B_{1CO} B_{hCO} - B_{hCO} B_{1HC}\} \quad (3)$$

$$Y_{CO} = \{B_{1HC} Iph - B_{hHC} Ipl\} / \{B_{1HC} B_{hCO} - B_{hHC} B_{1CO}\} \quad (4)$$

15. A catalyst diagnosis system comprising the gas composition sensor described in any one of the item 1 to the item 13 installed in the downstream side of a catalytic converter for purifying exhaust gas of an engine, a means for selectively measuring a concentration of hydrocarbon component in the exhaust gas in the downstream side of the catalytic converter using the above gas composition sensor at a pre-determined time after every starting of engine operation when it is judged that the engine has been warmed up under a predetermined condition in connection with a regulated test mode on engine bench, and a means for calculating a purifying ability of the catalytic converter by executing a series of statistical processing such as averaging and comparison of the measured value using pre-stored data.

16. A catalyst diagnosis system comprising the gas composition sensors described in any one of the item 1 to the item 13 installed between an exhaust gas manifold of an engine and a catalyst converter and between the downstream side of the catalyst converter and a muffler one for each, a means for selectively measuring purifying rates of hydrocarbon components in the exhaust gas in the upstream side and the downstream side of the catalytic converter using the above pair of gas composition sensors at a pre-determined time after every starting of engine operation when it is judged that the engine has been warmed up under a predetermined condition, and a means for calculating purifying rates in the upstream side and the downstream side of the catalytic converter by executing a series of statistical processing such as averaging and comparison of the measured values using pre-stored data.

17. A catalyst diagnosis system described in the item 16, which comprises a means for operating the gas composition sensor installed in the upstream side of the catalytic converter as an air-to-fuel sensor for air-to-fuel control by controlling temperature of the sensing element in the high temperature side of the gas composition sensor after a pre-determined time period of starting of engine operation.

18. A catalyst diagnosis method using the catalyst diagnosis system described in any one of the item 15 to the item 17, the method comprises the steps of measuring a concentration of hydrocarbon using the gas composition sensor in at least one sampling time of 10 to 120 seconds set in an operating interval of 450 seconds from starting of operation of the engine after an appropriate engine cooling process to completion of warming-up, performing an averaging process such as integration, comparison with an initial value and storing process of the measured data, and performing comparative diagnosis with a tolerable degradation level of purifying rate.

19. An air-to-fuel ratio control system for an engine using the gas composition sensors described in any one of the item 1 to the item 13, which comprises a means for selectively detecting hydrocarbon using a pair of sensing elements during warming-up after starting of engine operation and for performing operating correction control such as fuel supply control or ignition timing control by detecting an air-to-fuel ratio using the sensing element in the high temperature side.

20. An air-to-fuel ratio control system for an engine using the gas composition sensors described in any one of the item 1 to the item 13, which controls in such a manner that when a fuel supply system is shut off to stop the engine, an ignition system and the other related systems are shut off after burning fuel having been supplied to the engine.

21. An air-to-fuel ratio control system for an engine, which comprises the gas composition sensors described in any one of the item 1 to the item 13 in a position near an intake manifold assembly of the engine intake air system where exhaust gas recirculation gas and purged vapor fuel are merged, and a means for correcting an amount of fuel supply based on an air-to-fuel ratio signal obtained from a detected signal of a high temperature sensing element of the gas composition sensor.

22. An air-to-fuel ratio control system for an engine, which comprises the gas composition sensors described in any one of the item 1 to the item 13 in a position near an intake manifold assembly of the engine intake air system where exhaust gas recirculation gas and purged vapor fuel are merged, and a means for controlling an exhaust gas recirculation rate by calculating the exhaust gas recirculation rate from concentrations of mono-oxide carbon and hydrocarbon selectively obtained from the sensing element in the high temperature side and the sensing element in the low temperature side.

23. A fuel gas leakage detecting system, which is constructed in such that the gas composition sensors described in any one of the item 1 to the item 13 is used as a detecting means for detecting fuel gas leakage of fuel gas such as municipal gas, liquified petroleum gas, compressed natural gas or the like to operate an alarm, a safety valve and so on.

24. A fuel gas leakage detecting system, which is constructed in such that the gas composition sensors described in any one of the item 1 to the item 13 is used as a detecting means for detecting incomplete combustion of fuel gas such as municipal gas to selectively detect mono-oxide carbon, liquified petroleum gas, compressed natural gas or the like to operate an alarm, a safety valve and so on.

BRIEF DESCRIPTION OF THE DRAWINGS

FIG. 7 is a cross-sectional view showing the overall construction of the gas composition sensor of FIG. 1.

DETAILED DESCRIPTION OF THE PREFERRED EMBODIMENTS

Embodiments of the present invention will be described in detail below, referring to the accompanying drawings.

Figure 1:
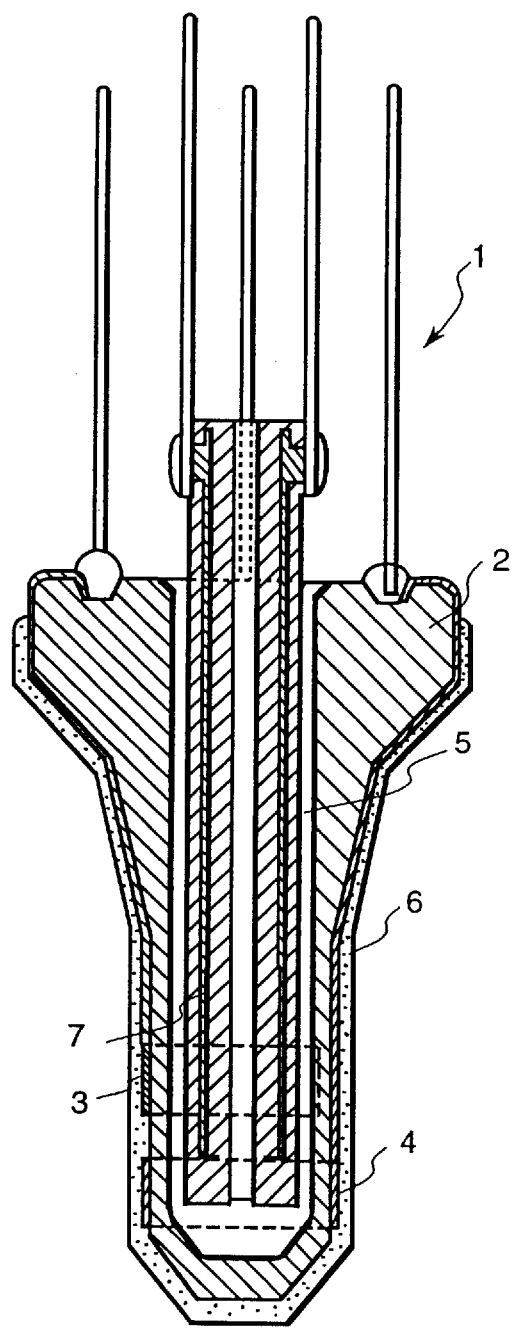
FIG. 1 is a sectional view of an embodiment of a gas composition sensor in accordance with the present invention.

FIG. 1 shows an embodiment of a gas composition sensor 1 in accordance with the present invention.

Referring to FIG. 1, the gas composition sensor 1 comprises a solid electrolyte body 2 the shape of which is a cylinder closed in its front end, a reference electrode 5 to be exposed to atmosphere arranged inside the cylinder of the solid electrolyte body 2, and a detecting electrode 3 in the high temperature side and a detecting electrode 4 in the low temperature side exposed to exhaust gas arranged in the outer front end of the cylinder of the solid electrolyte body 2. The cylindrical portion of the solid electrolyte body 2 is covered with a member for limiting diffusion of gas made of a porous film in order to cover the whole of the detecting electrodes 3, 4. The diffusion limiting member 6 limits velocity of exhaust gas diffusing up to the surfaces of the detecting electrodes 3, 4. Since the surroundings of the detecting electrodes 3, 4 are directly covered with the porous film of the diffusion limiting member, there is no gap in the member, which is different from covering with a single hole member. A heat generating body 7 is contained in the inner side space of the cylindrical solid electrolyte member 2 to heat the solid electrolyte body 2 from the inner side with radiant heat, and as a result the detecting electrodes 3, 4 are heated. One sensing element is composed of the solid electrolyte body 2, one of the detecting electrodes (3 or 4), the reference electrode 5 and the diffusion limiting member 6, and the gas composition sensor 1 is composed of the two sensing elements.

The fundamental construction of the gas composition sensor 1 is the same as that of an oxygen sensor which outputs a switching output signal at stoichiometric air-to-fuel ratio point. However, a different point is that the diffusion limiting film of the gas composition sensor 1 is close-grained (or dense) and thick (450 μm), but, on the other hand, the film of the oxygen sensor is a protective film and thin (50 μm).

Although FIG. 1 shows the cylindrical solid electrolyte body 2 having the closed front end, it is possible to employ a construction in which the heat generating body, the electrode and the solid electrolyte body are formed in flat-plate-shapes and laminated as to be described later. In a case of a laminating type sensor, instead of using atmospheric air as a reference oxygen partial pressure, it is possible to employ a construction in which a reference oxygen partial pressure is formed by pumping oxygen in an exhaust gas using a concentration cell. The embodiment of the present invention can be applied to either of the constructions.

Figure 2:
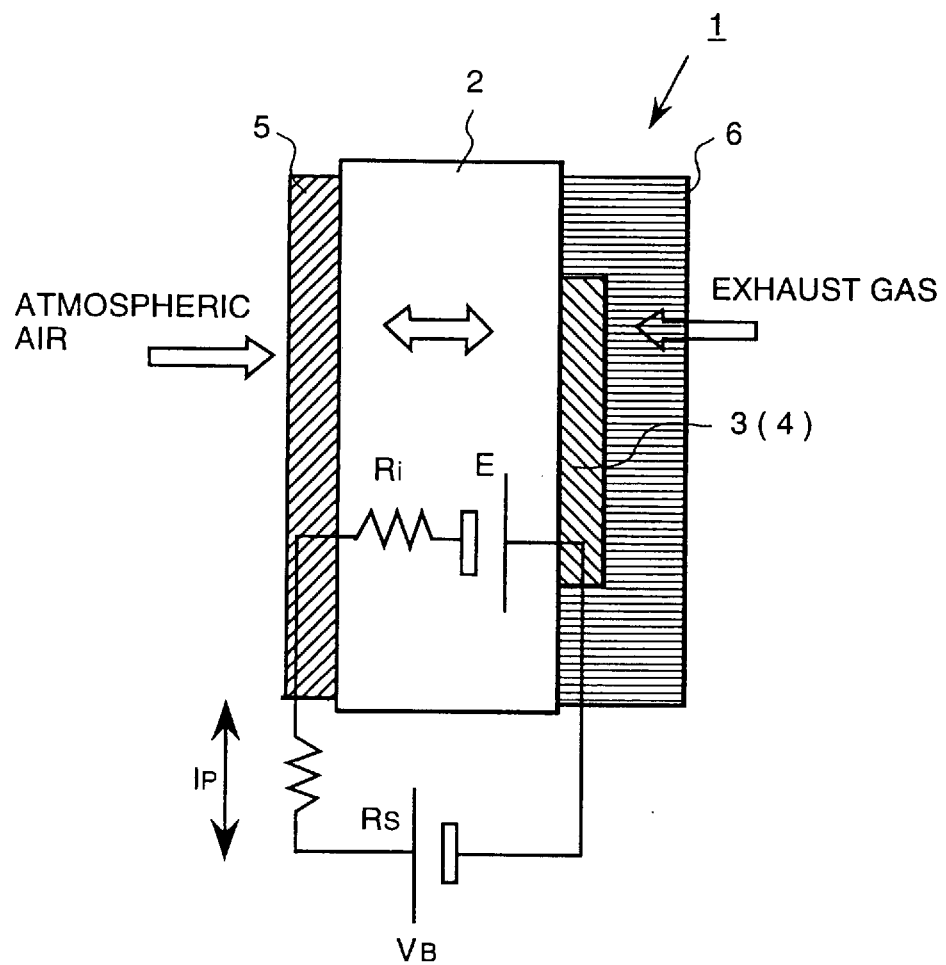
FIG. 2 is a view showing the operation principle of the gas composition sensor of FIG. 1.

FIG. 2 shows an electromotive force E induced between the reference electrode 5 and the each detecting electrode 3 (4) of an oxygen concentration cell exposed to atmospheric air and an exhaust gas in the gas composition sensor 1. The electromotive force E can be calculated by the following Nernst's equation (5).

$$E = RT/4 F \ln(Pa/Pd) = 0.0496 \ln(Pa/Pd), \tag{5}$$

where R is the gas constant, T is a temperature of the cell in kelvins (=1000K), F is Faraday's constant, Pd is an oxygen partial pressure around the detecting electrode and Pa is an oxygen partial pressure of the reference electrode.

By covering the surrounding of the detecting electrodes 3,4 with the diffusion limiting member 6 of a fine-grained porous film or a single-hole member, exhaust gas is once captured, and oxygen gas is accelerated to be ionized by catalytic function of platinum, and thereby the electromotive force shows a steep switching characteristic to the air-to-fuel ratio. By maintaining the peripheral portion of the detecting electrodes 3, 4 in a thin oxygen state by pumping oxygen, exhaust gas is rate-determined to freely diffuse toward the detecting electrodes 3, 4 by the diffusion limiting member 6. Therefore, by pumping the rate-determined oxygen gas flowing from the exhaust gas and by measuring the pumped oxygen ions as a current, the current indicates an concentration of oxygen in the exhaust gas, that is, an air-to-fuel ratio.

A diffusion flow rate is determined by setting a shape of the single holes of the diffusion limiting member 6, and can be measured as an oxygen diffusion current Ip. The oxygen diffusion current Ip can be expressed by the following equation (6).

$$Ip = 4FD(Pe-Pd)/RT \times s/l, \tag{6}$$

where Ip is the oxygen diffusion current, D is a diffusion coefficient of various exhaust gas components, s/l is a ratio of a cross-sectional area s of a passage to a length l of the passage when the diffusion limiting member is equivalently expressed by a single hole having the cross-sectional area s of the passage to the length l of the passage, and Pe is an oxygen partial pressure in the exhaust gas.

Referring to FIG. 2, in order to maintain the electromotive force E of the concentration cell, the diffusion rate-determined oxygen in the exhaust gas is allowed to flow in the both directions toward the reference electrode 5 and the detecting electrodes 3 (4) as ion current Ip. For doing so, a driving voltage $V_B$ is negative-feedback-controlled. Therein, the following equation (7) is satisfied.

$$V_B = E + Ip(Ri + Rs), \quad (7)$$

where Ri is an internal resistance of the concentration cell, and Rs is a resistance of a resistor for measuring Ip.

A member 6 for limiting diffusing exhaust gas, that is, a porous film or a single-holes member is formed around the detecting electrode of the concentration cell which is composed of the solid electrolyte body 2 having conductivity for oxygen ions and the opposite platinum electrode having catalytic function. The concentration cell, that is, the detecting electrodes 3, 4 are stably heated by the adjacent heat generating body 7 up to temperatures capable of conducting the pumping current. In more detail, a heater power source for the heat generating body is negative-feedback-controlled so that resistance between the electrodes becomes, for example, 20Ω constant. By pumping oxygen around the detecting electrodes 3, 4 toward the reference electrode side, the pumping current Ip is controlled in the both direction so that the electromotive force E of the concentration cell becomes E=0.571V in the Nernst's equation (5). Therein, the ratio of the oxygen partial pressure Pa to the oxygen partial pressure Pd around the detecting electrodes 3, 4 always maintained at a state of $Pa/Pd = 10^5$. That is, $Pa = 2.09 \times 10^{-1}$ and $Pd = 2.09 \times 10^{-6}$. Therein, the oxygen ion current of the diffusion rate-determined oxygen entering around the detecting electrodes 3, 4 from the exhaust gas becomes a signal having a proportional relationship to the air-to-fuel ratio.

Description will be made below on how the gas composition sensor 1 detects the gas compositions when there are oxygen and combustible gas components such as hydrocarbon, mono-oxide carbon and so on.

The combustible gas compositions diffuse around the detecting electrodes 3, 4 of the concentration cell which are stably heated to temperatures high enough to cause oxidizing reaction, and each of the hydrocarbon and the mono-oxide carbon is reacted with the oxygen by the catalytic function of the platinum electrodes. When remaining oxygen in the exhaust gas is consumed in the oxidization, oxygen is additionally transferred from the atmosphere side in a form of ion current Ip in order to maintain the electromotive force E constant. The amount of the current is equivalent to the sum of the surplus combustible components of hydrocarbon and mono-oxide carbon which have not been oxidized with the oxygen in the exhaust gas side. In other words, the oxygen and the combustible components such as hydrocarbon and mono-oxide carbon in the exhaust gas side firstly react with each other in the gas composition sensor, and surplus combustible components are measured as the oxygen ion current Ip when the surplus combustible composition exist. However, the hydrocarbon is not solely measured by being separated from the mono-oxide carbon.

The key point of the present embodiment is that by taking advantage of a characteristic that each of compositions such as mono-oxide carbon, hydrocarbon and so on composing a combustible gas has an intrinsic oxidizing reaction temperature, each concentration of the gas components is obtained by solving simultaneous equations with two unknowns using two total oxygen ion current values measured by two detecting electrodes having different temperatures, that is, two sensing elements each of which has one or the other of the two electrodes in different temperatures to each other.

Figure 3:
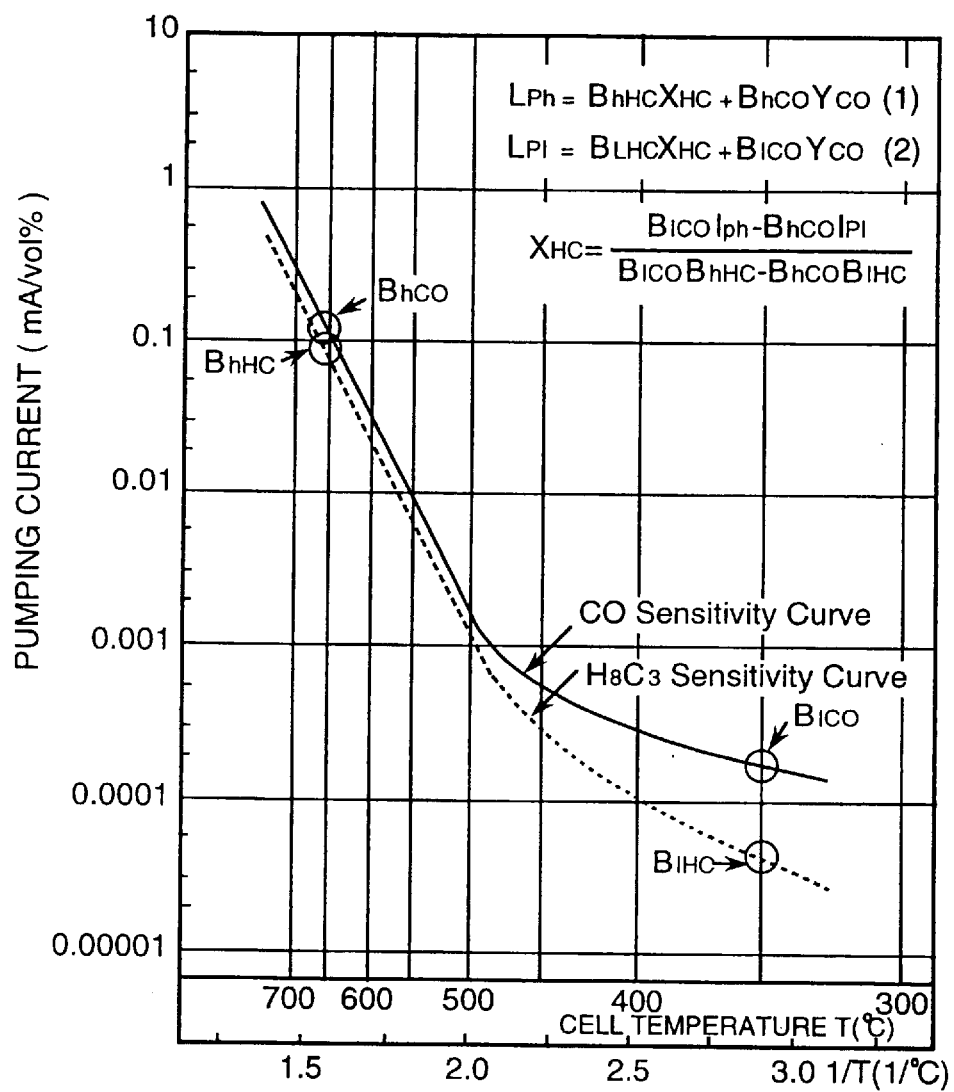
FIG. 3 is a graph showing the correlation between gas sensitivity coefficient and sensing element temperature of the gas composition sensor of FIG. 1.

FIG. 3 shows the relationships between measured sensitivities to hydrocarbon and mono-oxide carbon and temperature of detecting electrodes of a concentration cell. Measurement was conducted using calibration gases respectively diluting $H_8C_3$ (propane) and mono-oxide carbon with nitrogen of 3 vol % and 40 vol % and setting controlled temperatures of a pair of sensing elements to Th=650° C. and Tl=350° C. The following results of oxygen ion current Ip per unit gas concentration, that is, gas current sensitivity were obtained.

650° C. 350° C.

$H_8C_3$: 0.09 mA/vol % 0.00004 mA/vol % CO: 0.13 mA/vol % 0.00024 mA/vol %

That is, the result means that concentrations of hydrocarbon and mono-oxide carbon can be separately measured by taking advantage of difference in relationships between temperature of the detecting electrode in the concentration cell and the detecting sensitivity for hydrocarbon and monooxide carbon, that is, difference in temperature dependence of gas detecting sensitivity for hydrocarbon and mono-oxide carbon. It is necessary to measure the sensitivity using an actual exhaust gas at actual temperature of the sensing element since molecular weight of hydrocarbon after combustion is small.

Further, as for how much the temperature difference between the detecting electrodes 3, 4 should be set, since the difference in gas detecting sensitivities for hydrocarbon and mono-oxide carbon is required to be large to a certain degree, it is preferable in taking various kinds of combustion into consideration that the temperature of the detecting electrode in the low temperature side is not higher than 450° C. and the temperature difference between the two detecting electrodes in the high temperature side and in the low temperature side is not smaller than 100° C.

Description will be made on a case where the gas composition sensor is applied to diagnosis of catalyst for an engine.

A reference level of diagnosis of catalyst for an engine mounted on a vehicle is defined as 1.5 times of regulated value of hydrocarbon measured by the CVS method under a pre-determined operating mode of engine. The diagnosis of catalyst for an engine mounted on a vehicle is a pre-diagnosis for an exhaust gas test under a legal operation mode based on the exhaust gas regulation.

Figure 4:
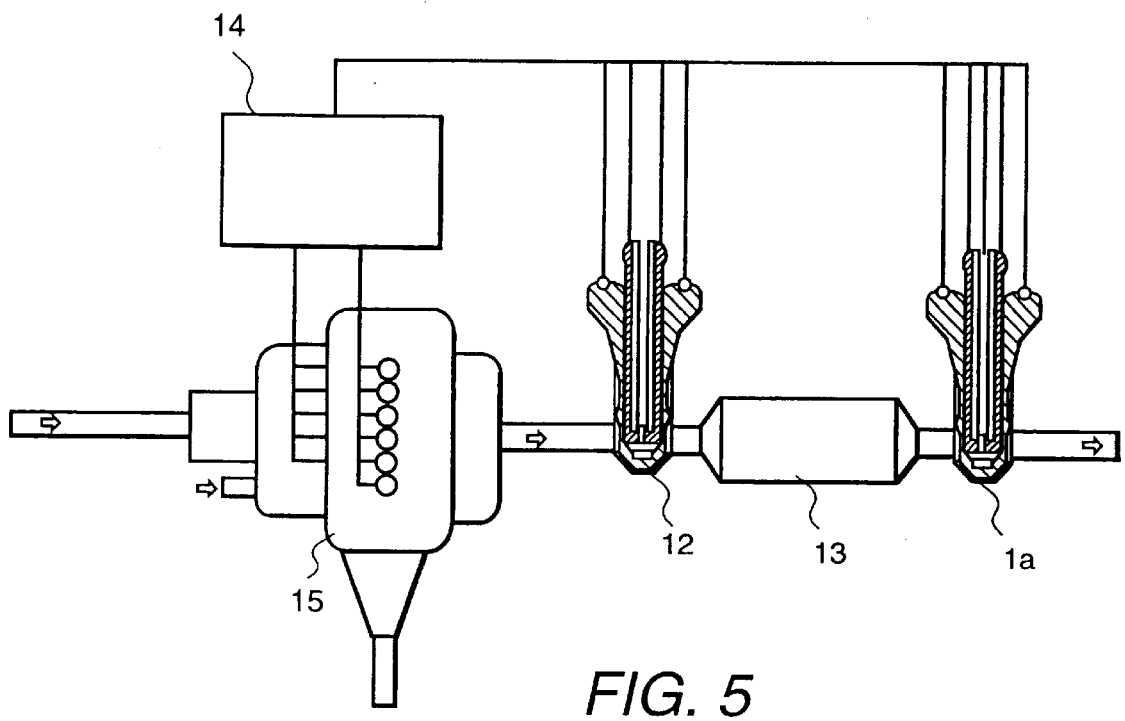
FIG. 4 is a view showing an arrangement of a catalyst diagnosis system for an engine having the gas composition sensor of FIG. 1.

In FIG. 4, a catalytic converter 13 is arranged in a exhaust pipe of the engine 15, and an air-to-fuel ratio sensor 12 having one sensing element (one detecting electrode 4) is arranged in the upstream side of the catalytic converter 13 and a gas composition sensor 1a is arranged in the downstream side of the catalystic converter. Degradation in performance of the catalytic converter 13 is diagnosed through calculation using a controller or electronic controller 14 based on measured results of the gas composition sensor.

The gas composition sensor 1a comprises a plug containing two sensing elements each of which has one or the other of a pair of detecting electrodes 3, 4 having different temperatures to each other, the gas composition sensor being installed in the position downstream side of the catalytic converter 13, the engine 15 being operated so as to correspond to a regulated test mode operating condition, concentration of hydrocarbon being calculated using the signals from the gas composition sensor to diagnose degradation of the catalytic converter 13.

There is assumed a case where an engine is started in a pre-determined operation without any disturbance by an operator such as accelerator operation even by adding a kind of disturbance limiting function if necessary, for example, such as start idling operation with throttle valve fully closed. In starting of an engine with throttle valve fully closed, during a period for approximately 60 seconds after just starting of the engine, a volume of hydrocarbon and mono-oxide carbon in nearly the same order of the total displacement volume of the engine is exhausted. A concentration of hydrocarbon can be measured using the gas composition sensor 1a described above in the initial period of starting the engine, but cannot be detected after completion of warming-up because the concentration of hydrocarbon becomes too low to be detected. Therefore, a precondition for satisfying the present embodiment is that the purifying capability of the catalyst during the initial period of starting the engine when temperature of the catalyst is low is correlated with the purifying capability during regulated mode operation. The present embodiment has been experimentally confirmed to satisfy the precondition.

Further, in order to perform measurement of exhaust gas after being purified using the gas composition sensor 1a installed in the downstream of the catalytic converter 13, it is necessary that the engine satisfies a pre-determined initial condition before starting and reproducibility in exhaust gas is obtained. For example, the condition is that the engine and the catalyst 13 are sufficiently cooled and the temperature condition at the time when the engine is started into operation is within a pre-determined range.

As for a precondition for the gas composition sensor 1a, measurable exhaust gas temperature at starting the engine must be lower than the setting temperature of the sensing element 4 in the low temperature side. At that time, both of the two detecting electrodes 3, 4 must be started so as to meet the time period for measuring.

Figure 5:
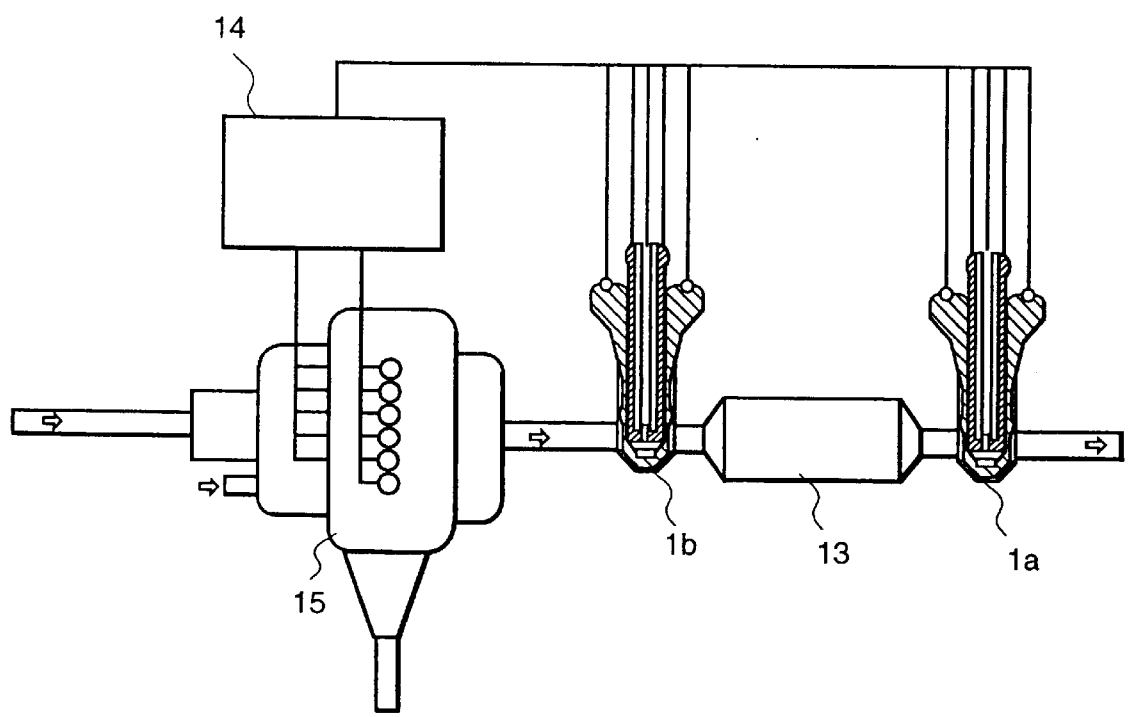
FIG. 5 is a view showing another arrangement of a catalyst diagnosis system for an engine having the gas composition sensor of FIG. 1.

FIG. 5 shows a construction where the air-to-fuel sensor 12 of FIG. 4 is replaced by a gas composition sensor 1b which has the same construction as that of the gas composition sensor 1a arranged in the downstream of the catalytic converter 13.

Since compositions of hydrocarbon at the upstream side and the downstream side of the catalytic converter 13 are measured in the construction shown in FIG. 5, degradation of the catalytic converter 13 can be diagnosed from the ratio. In this case, it is necessary to determine degradation level by clarify the relationship between the regulated value of the diagnosis system and the purifying rate in advance. That is, the gas composition sensors 1a, 1b are respectively arranged at the upstream side and the downstream side of the catalytic converter 13 of the engine 15, and a purifying capability of hydrocarbon of the catalytic converter 13 is obtained from both of the detected value detected by both of the gas composition sensors 1a, 1b, and diagnosis of the catalytic converter is performed by calculating a departure ratio from the exhaust gas regulated value using a degradation degree from an initial detected value. As for a precondition in this case, it is necessary to obtain the relationship between the measured value obtained through the CVS method according to the operating mode and this purifying capability in advance.

Figure 6:
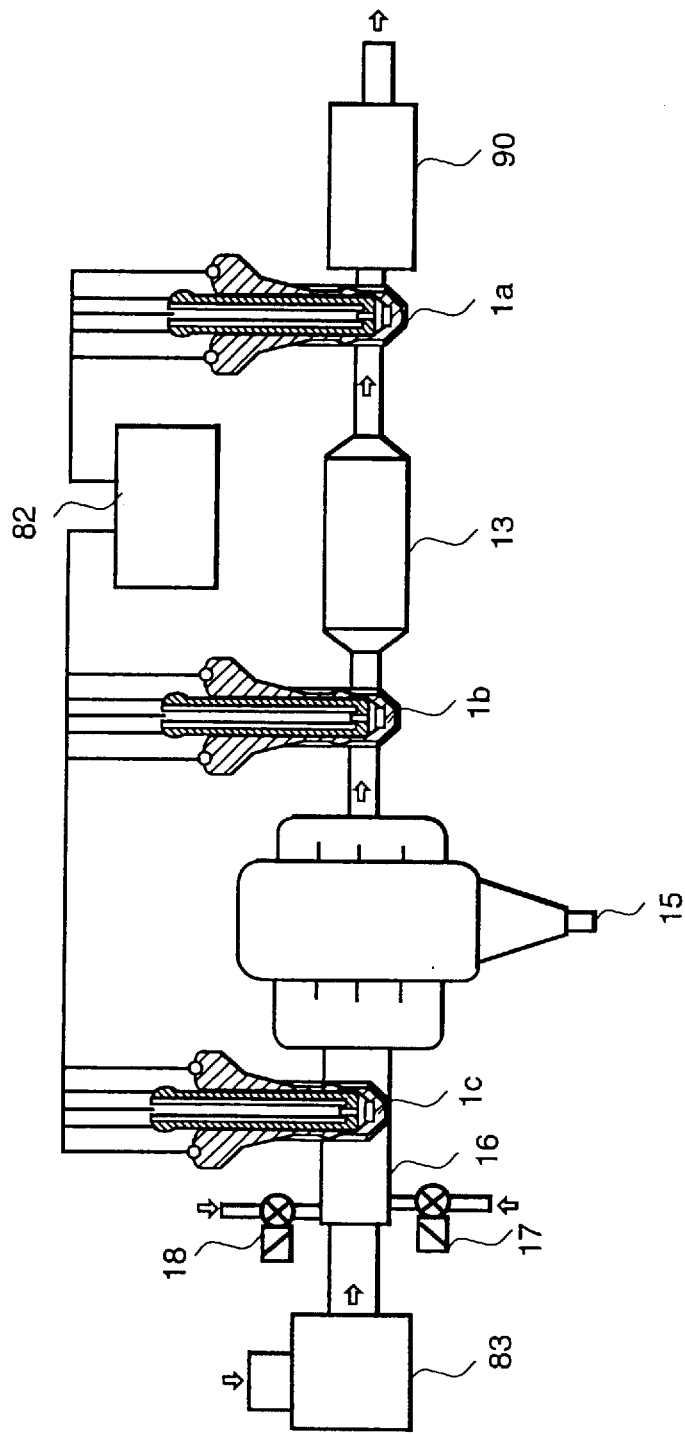
FIG. 6 is a view showing a further arrangement including a catalyst diagnosis system for an engine having the gas composition sensor of FIG. 1 and other components.

FIG. 6 shows a construction in which three gas composition sensors 1a, 1b, 1c composed of a pair of detecting electrodes 3, 4 are respectively arranged in three portions of an intake manifold 16 of an engine 15, and the upstream side and the downstream side of a catalyst converter 13. The gas composition sensor 1c detects a mixing ratio of exhaust gas and fuel vapor controlled to flow into the engine by an exhaust gas recirculation control valve 17 and a fuel vapor purge valve 16 to perform critical control or optimum control of the exhaust gas recirculation ratio and to correct the intake air-to-fuel ratio at purging.

The oxygen and combustible gases can be separately measured using a pair of sensing elements each of which has one or the other of the detecting electrodes 3, 4, (1) by utilizing difference in flowing directions of oxygen ions induced by between the oxygen and the combustible gases such as hydrocarbon and mono-oxide carbon, and (2) by utilizing difference in oxidizing catalytic capabilities depending on temperature of the sensing element. Further, more suitable control can be performed (3) by employing time-sharing sequence, and (4) by taking opening-and-closing timing of the control valves 17, 18 and time required for flowing into consideration.

FIG. 7 is a schematic assembling view of the gas composition sensor 1. The test-tube-shaped gas composition sensor 1 of FIG. 1 is assembled in a plug body 42 and exhaust gas and atmospheric air are sealed with gaskets 44 and 45. A heater holding body 46 is bonded to a supporting body 50, and the gas composition sensor 1 and the heater holding body 46 are press-fastened by a spring washer 48 through a cover 47. Two lead wires from the heater holding body 46 and two lead wires from the detecting electrodes 3, 4 are press-crimped to clad wires 49 to be connected to an external connector. A protective cover 43 reduces exhaust gas flow speed to protect the top front end of the gas composition sensor 1 composed of the two sensing elements having the detecting electrodes 3, 4.

Figure 8:
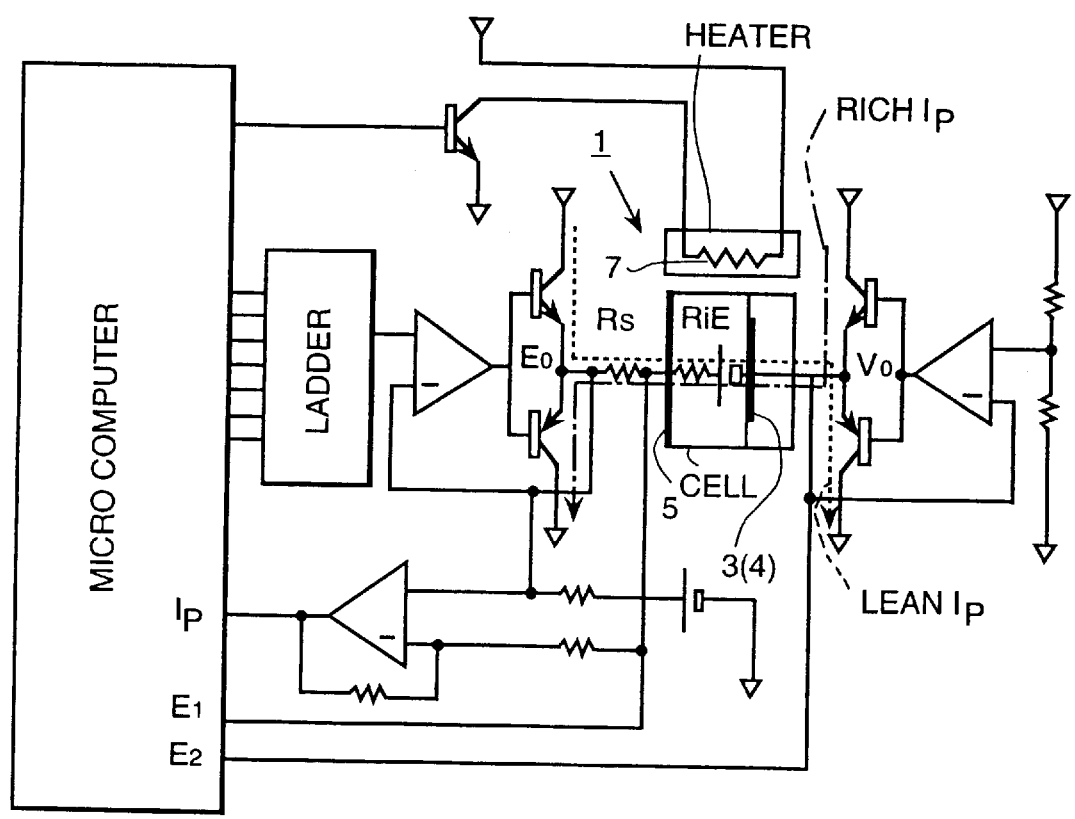
FIG. 8 is a diagram showing a sensing element and a control circuit for a heater of the gas composition sensor of FIG. 1.
Figure 9A:
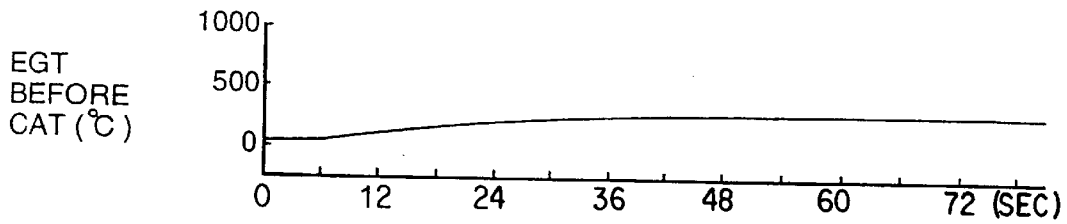
FIG. 9 is a measuring chart by the gas composition sensor in the downstream side of the catalytic converter of FIG. 1 and an exhaust gas analyzer.
Figure 9B:
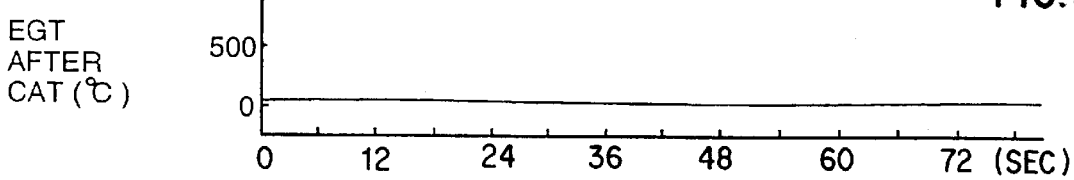
Figure 9C:
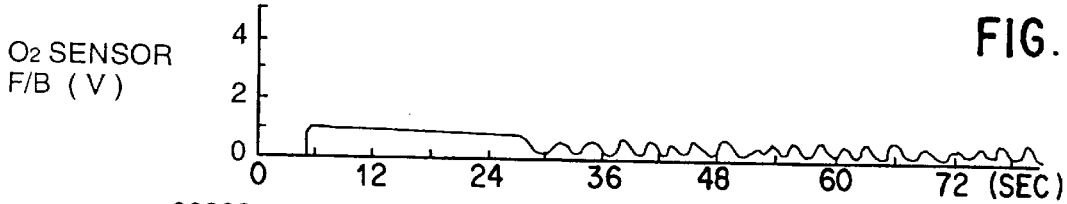
Figure 9D:
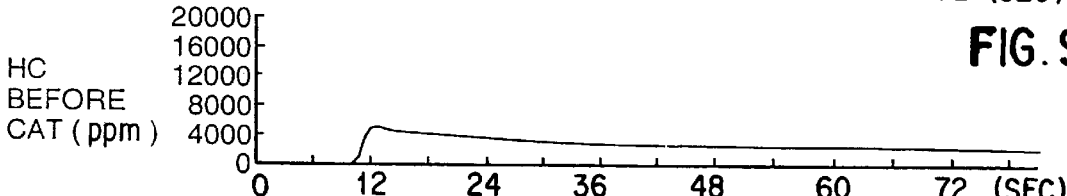
Figure 9E:
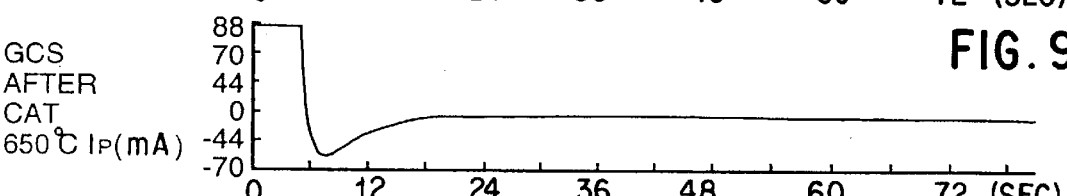
Figure 9F:
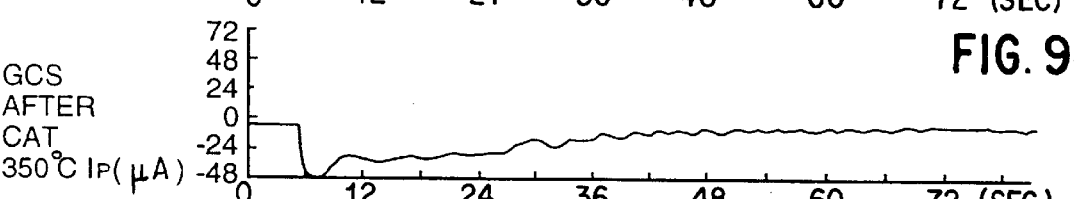
Figure 9G:
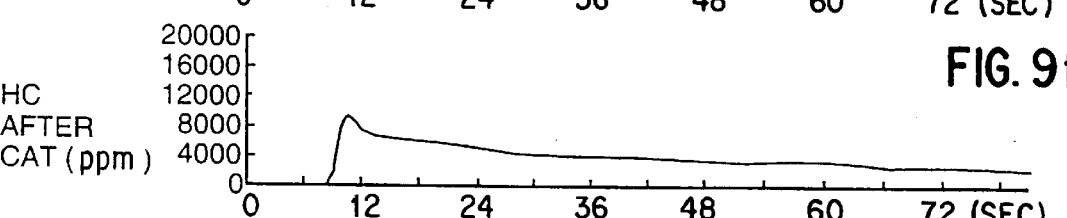
Figure 9H:
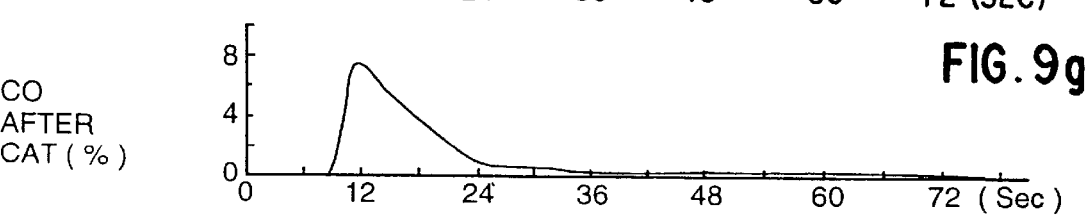

FIG. 8 shows an embodiment of a circuit for driving one gas composition sensor 1 which comprises the sensing element having a concentration cell composed of the reference electrode 5 and the detecting electrodes 3, 4 and the diffusion limiting body (film), and the heat generating body 7. Outline of the operation is that an electromotive force E is maintained at a constant value of 0.458 V by conducting oxygen ion current in the detecting electrodes 3, 4 in the both directions using oxygen of atmosphere and exhaust gas. Therein, the oxygen concentration near the detecting electrodes 3, 4 exposed to the exhaust gas is controlled by negative feed-back so as to be $2.09 \times 10^{-11}$ whereas the oxygen concentration of the reference electrode 5 exposed to atmosphere is $2.09 \times 10^{-1}$. In order to stably control temperature of the sensing element at 650° C., an internal resistance Ri=20Ω of the sensing element is measured from voltage drop by a voltage between the both terminals of the cell and the oxygen ion current. The oxygen ion current Ip of a gas composition signal is converted into a voltage by a measurement resistor Ri. The analog signals of E, Ri, Ip are A/D-converted to be processed calculation in a micro-computer, and then D/A-converted again by a rudder to form a negative feed-back circuit. The character LEAN Ip in the figure indicates a branching path for conducting current of residual oxygen when the air-to-fuel ratio is lean, and the character RICH Ip in the figure indicates a branching path for conducting current of oxygen to oxidizing combustible composition at the detecting electrode when the air-to-fuel ratio is rich.

FIG. 9 is a chart for obtaining a correlation between values Iph, Ipl in relation with hydrocarbon and mono-oxide carbon measured by the gas composition sensor 1 and values $G_{HC}$, $G_{CO}$ measured by an exhaust gas analyzer used as a standard equipment. In the catalyst diagnosis system constructed in as shown in FIG. 4, the detecting accuracy when hydrocarbon and mono-oxide carbon are measured using the gas composition sensor 1a in the downstream side of the catalytic converter 13 is compared with the measured result by the exhaust gas analyzer.

The engine 15 is warming-up-operated at a speed of 1400 rpm after being started, and the pair of detecting electrodes 3,4 are heated and stably maintained at Th=650° C. and Tl=350° C., respectively. The chart shows analog wave-forms of oxygen ion currents (mA) Iph, Ipl and exhaust gas components (%) $G_{HC}$, $G_{CO}$ in the above condition.

Here, a concentration $X_{HC}$ of hydrocarbon group component and a concentration $Y_{CO}$ of the other component such as mono-oxide carbon are obtained by the following simultaneous equations (1), (2) using four sensitivity coefficients $B_{hHC}$, $B_{hCO}$, $B_{1HC}$, $B_{1CO}$ which separate a gas composition into hydrocarbon group component and the other components such as mono-oxide carbon and have been experimentally determined in advance. It was confirmed whether or not the essential feature of the embodiment of the present invention was satisfied by comparing the solutions with the values $G_{HC}$, $G_{CO}$.

$$Iph = B_{hHC} X_{HC} + B_{hCO} Y_{CO} \quad (1)$$

$$Ipl = B_{1HC} X_{HC} + B_{1CO} Y_{CO} \quad (2)$$

Therein, Iph, Ipl are measured values and $B_{hHC}$, $B_{hCO}$, $B_{1HC}$, $B_{1CO}$ are measured values using a reference gas in advance. However, since propane is used as the hydrocarbon, the molecular weight is higher than the molecular weight of hydrocarbon in an actual combustible gas. $X_{HC}$ and $Y_{CO}$ are solutions obtained by solving the simultaneous equations and expressed by the following equations (3), (4). The solution is compared with the values $G_{HC}$, $G_{CO}$ obtained from the exhaust gas analyzer.

$$X_{HC} = \{B_{1CO} Iph - B_{hCO} Ipl\} / \{B_{1CO} B_{hHC} - B_{hCO} B_{1HC}\} \quad (3)$$

$$Y_{CO} = \{B_{1HC} Iph - B_{hHC} Ipl\} / \{B_{1HC} B_{hCO} - B_{hHC} B_{1CO}\} \quad (4)$$

The abscissas of the test chart of FIG. 9 indicate elapsing time after starting of the engine. Explaining the wave-forms in descending order, the wave-forms (a) and (b) are exhaust gas temperatures at the upstream side and the downstream side of the catalytic converter, respectively, and the wave-form (c) is an output signal of the oxygen sensor 12 and the time band of periodically switching of lean-and-rich indicates that the intake gas is controlled in stoichiometric air-to-fuel ratio.

The wave-forms (d) and (g) are amounts (ppm) of exhausted hydrocarbon at the upstream side and the downstream side of the catalytic converter, respectively, and a peak in each of the wave-forms is observed just after starting of the engine. The peak of the hydrocarbon concentration in the upstream side of the catalytic converter appears at 13 seconds, and the peak of the hydrocarbon concentration in the downstream side of the catalytic converter appears at 10 seconds. It can be understood from the result that the peak of the hydrocarbon concentration in the upstream side of the catalytic converter is produced by combustible composition at starting of the engine, and the difference between the peak of the hydrocarbon concentration in the downstream side of the catalytic converter and the peak of the hydrocarbon concentration in the upstream side is produced by that the combustible composition exhausted at stopping of the engine in the precedent time and accumulated in the catalyst is exhausted due to temperature rise of the catalyst by starting of the engine in this time. The amount of the combustible composition exhausted at stopping of the engine can be decreased by improving stopping operation of the engine. In a conventional procedure of switching-off a key switch to stop engine operation, a fuel supply system and an ignition system are switched off nearly at the same time. Whereas, in order to decrease the amount of combustible composition, the fuel supply system is shut off first, then the ignition system is shut off, and these timings are optimized. By doing so, it is possible to decrease an exhausting amount of combustible component at the following engine starting. This feature is the same in case of mono-oxide carbon. Therefore, the peaks in the exhausting amounts (ppm) of hydrocarbon and mono-oxide carbon are nearly in synchronism with each other and appear at elapsing time of 10 to 12 second after engine starting.

The wave-forms (e) and (f) are currents Ip of the gas composition sensor 1. Both of the currents Ip of the detecting electrodes 3, 4 set to temperatures of 650° C. and 350° C. do not have sampling delay due to a cooled state which is observed in the exhaust gas analyzer. The wave-form (h) is concentration of mono-oxide carbon in the downstream side of the catalytic converter. The peaks in both of the concentrations of hydrocarbon and mono-oxide carbon appear at a time around 8 second after starting of the engine. In the current wave-form of the sensing element set to 350° C., there is observed fluctuation having the same frequency as in the output of the oxygen sensor 12 superposed on the current wave-form.

Figure 10:
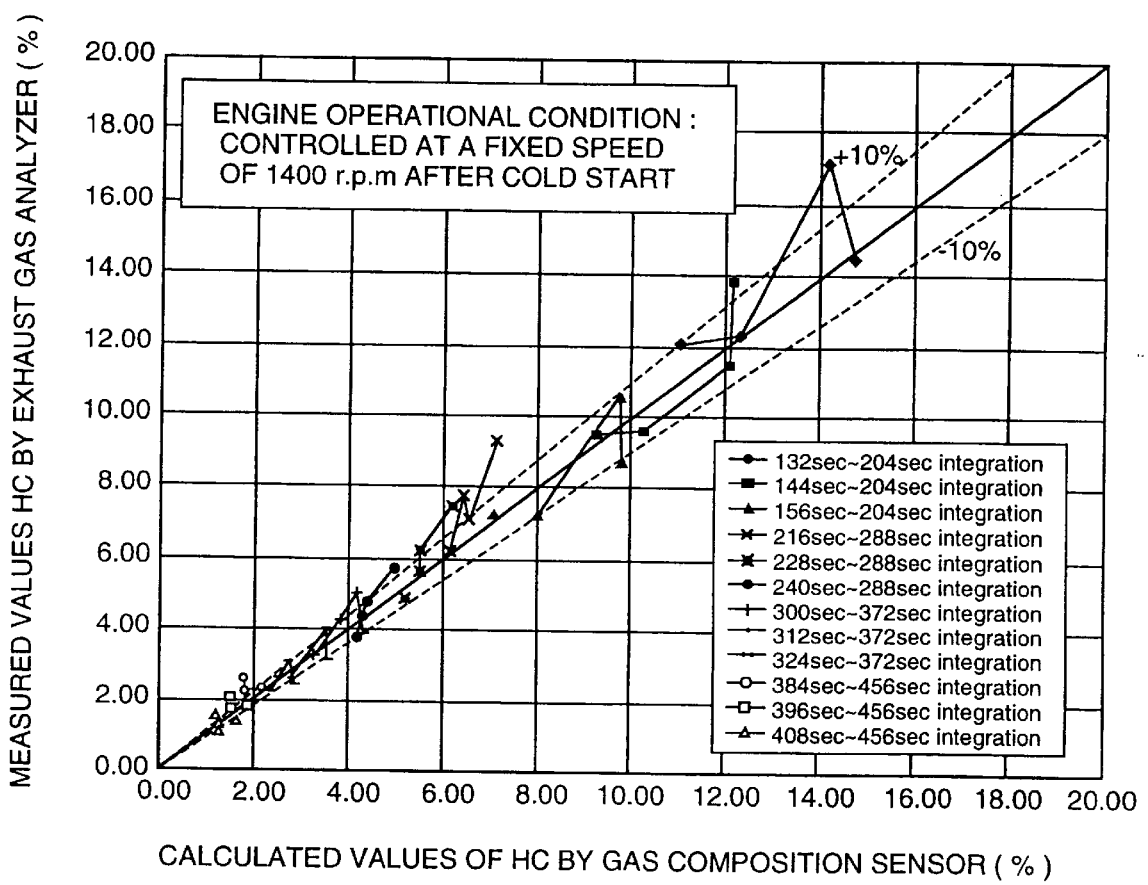
FIG. 10 is a graph showing the correlation between the gas composition sensor in the downstream side of the catalytic converter of FIG. 1 and the exhaust gas analyzer.

FIG. 10 shows the relationship between the calculated value of hydrocarbon by time band obtained from the result of FIG. 9 and the measured value of the exhaust gas analyzer. As the integration time band shifts to more elapsed-time side from starting of the engine, the error in the read values comes within the range of ±10% shown by dot lines in the figure. Although it is not shown in the figure, the error is large when the integration time band is less than 130 seconds of elapsed-time from starting of the engine. The reason may be that the effect of the peaking due to the combustible composition in the initial period of starting the engine continues until nearly 130 seconds after starting. Therefore, it is preferable that such an optimum integration time band is obtained for each type of engines in order to attain an accuracy having an error less than 10%.

Figure 11:
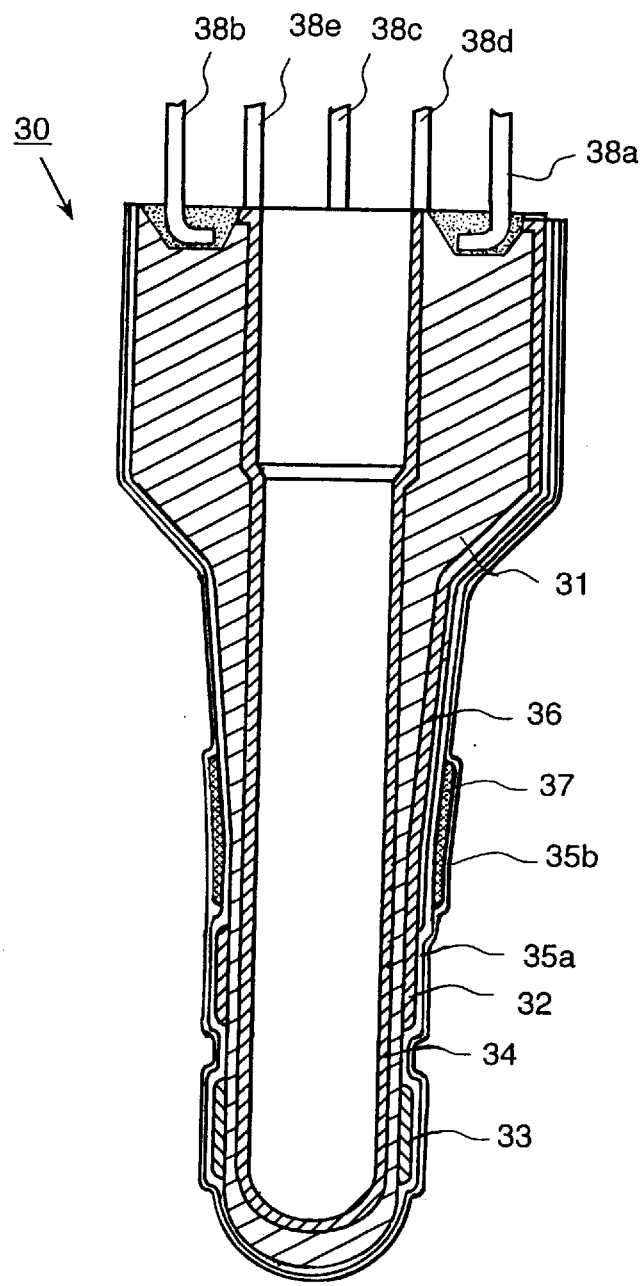
FIG. 11 is a cross-sectional conceptual view showing another embodiment of a gas composition sensor in accordance with the present invention.

FIG. 11 shows another (second) embodiment of a gas composition sensor 30 in accordance with the present invention. Two detecting electrodes 32, 33 having different temperatures are arranged in the outside of a zirconia solid electrolyte body 31 of the gas composition sensor 30 to form a construction containing a pair of sensing elements in one plug. The detecting electrode 32 in the high temperature side is exposed to an exhaust gas and the detecting electrode 33 in the low temperature side is also exposed to the exhaust gas. A reference electrode 34 is commonly used to the detecting electrodes 32, 33 and is exposed to atmosphere. A heat generating body 37 is arranged outside the zirconia solid electrolyte body 31 and at a position nearer to the base portion of the zirconia solid electrolyte body than the positions of the detecting electrodes 32, 33 to heat both of the detecting electrodes 32, 33. A gas tight layer 36 such as a glass layer covers and seals the base portion of the test-tube-shaped zirconia solid electrolyte body 31. A diffusion limiting layer 35a covers the surfaces of the detecting electrodes 32, 33 to limit diffusion of gas to the detecting electrodes 32, 33. A heat insulating layer 35b thermally insulates the heat generating body 37 and is made of the same material as that of the diffusion limiting layer 35a. Lead terminals 38a to 38e are provided in the end of the base portion of the gas composition sensor 30, the lead terminal 38a is connected to the detecting electrode 32 in the high temperature side, the lead terminal 38b is connected to the reference electrode 34, the lead terminal 38c is connected to the detecting electrode 33 in the low temperature side, and the lead terminals 38d and 38e are connected to the heat generating body 37.

The heat generating body 37 is heated up to nearly 700° C. to heat the detecting electrode 32 in the high temperature side to 650° C. and the detecting electrode 33 in the low temperature side to 350° C. by heat conduction. Both of the detecting electrodes 32, 33 can be stably heated to the respective required temperatures by optimizing the positional relationship to the commonly used heat generating body 37 and performing negative feed-back.

Figure 12:
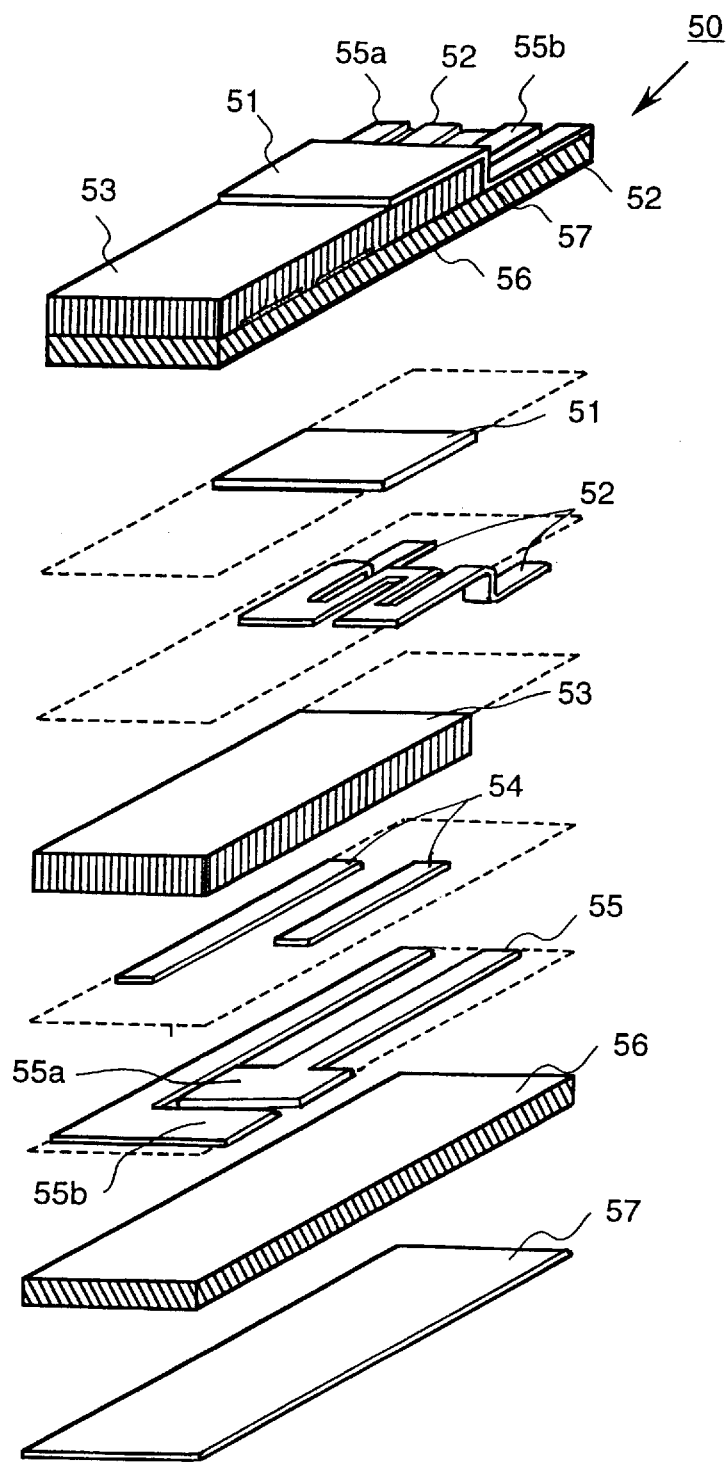
FIG. 12 is a conceptual view showing a laminate structure of a further embodiment of a gas composition sensor in accordance with the present invention.

FIG. 12 shows a further (third) embodiment of a gas composition sensor in accordance with the present invention. The gas composition sensor 1 of the first embodiment shown in FIG. 1 is cylindrical test-tube-shaped, whereas the gas composition sensor of the third embodiment is flat-plate laminated-layer-shaped. FIG. 12 is a perspective view showing the construction of the laminated-layer-shaped gas composition sensor in detail.

The basic operation of the third embodiment of the gas composition sensor 50 is the same as that of the first embodiment of the gas composition sensor 1, though they are different in shape. Referring to FIG. 12, a reference electrode 57 exposed to atmosphere is arranged on the bottom surface of a solid electrolyte body 56 of a substrate, and a detecting electrode 55a in the high temperature side exposed to an exhaust gas and a detecting electrode 55b in the low temperature side exposed to an exhaust gas are arranged on the top surface of the solid electrolyte body 56. Upper portions of both of the detecting electrodes 55a, 55b are covered with a sealing glass layer 54 to seal the lead portions of the detecting electrodes 55a, 55b so as to be not exposed to the exhaust gas. A porous ceramic diffusion limiting body (film) 53 is arranged to cover the whole upper portion of the solid electrolyte body 56, and a heat generating body 52 is arranged on the upper portion of the diffusion limiting body (film) 53. Outside the heat generating body 52, a heat insulating layer 51 is laminated to insulate heat between the heat generating body 52 and the external detected gas.

Although the present invention has been described in its embodiments in detail, it is understood that the present invention is not limited to the aforementioned embodiments and various modifications may be designed without departing from the spirit of the invention described in the claim.

For example, the laminating construction of the gas composition sensor in accordance with the present invention may be modified to other various embodiments as shown in FIG. 13(a) to (m).

Referring to FIG. 13, the laminated layer construction of the gas composition sensor can be basically expressed by two constructions. As shown in FIG. 13(a), one is a first laminated layer construction which is constructed with a heater A composed of a heat insulating layer 61, a heat generating body 62 and an insulator layer 63, and a sensing element B composed of a diffusion limiting layer 64, a detecting electrode 65, a solid electrolyte body 66 and a reference electrode 67 exposed to atmospheric air introduced as reference air; and as shown in FIG. 13(b), the other is a second laminated layer construction which is constructed with a heater A, a reference element C composed of a close-grained layer 68, a reference electrode 69, a solid electrolyte body 70 and a first pumping electrode 71, and a sensing element D composed of a diffusion limiting layer 72, a detecting electrode 73, a solid electrolyte body 74 and a second pumping electrode 75.

Figure 13A:
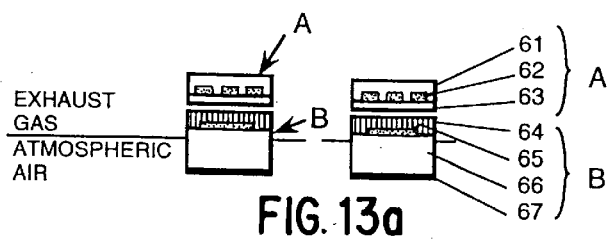
FIG. 13 shows conceptual views showing laminate structures of various embodiments of gas composition sensors in accordance with the present invention.
Figure 13B:
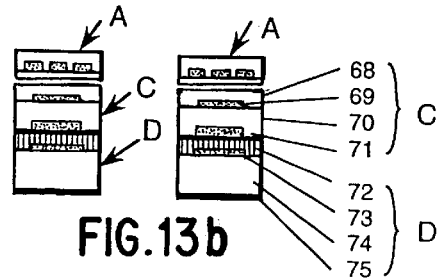
Figure 13C:
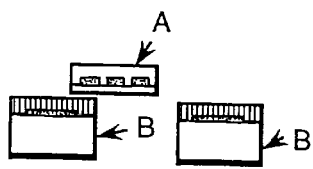
Figure 13D:
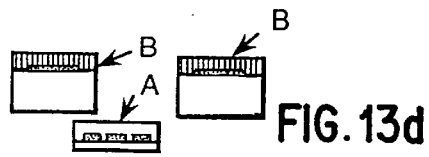
Figure 13E:
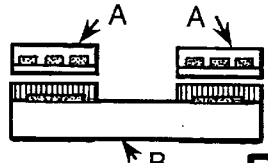
Figure 13F:
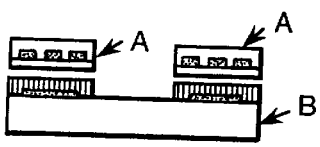
Figure 13G:
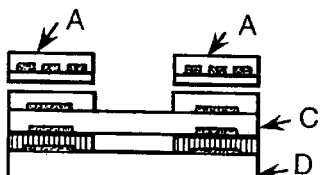
Figure 13H:
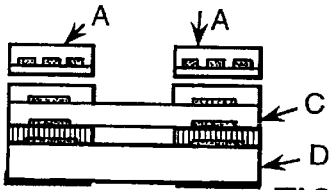
Figure 13I:
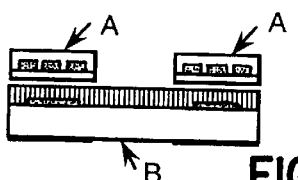
Figure 13J:
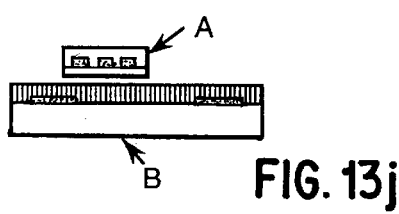
Figure 13K:
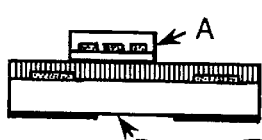
Figure 13L:
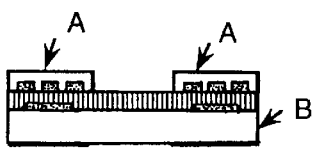
Figure 13M:
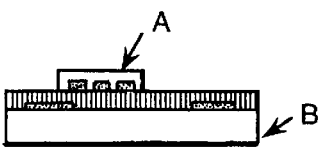

The whole construction of laminated layer of the gas composition sensor of FIG. 13(a) is formed by providing two of the first laminated layer constructions, and the whole construction of laminated layer of the gas composition sensor of FIG. 13(b) is formed by providing two of the second laminated layer constructions and is different from the laminated layer construction of the gas composition sensor of FIG. 13(a).

Different from the operation principle of the first laminated layer construction, the operation principle of the second laminated layer construction of FIG. 13(b) is that there are provided two concentration cells, the reference element C and the sensing element D, and the lower side concentration cell of the sensing element D detects oxygen or combustible composition in an exhaust gas entering through the diffusion limiting layer. The upper side concentration cell of the reference element C generates a reference oxygen concentration by pumping oxygen in the exhaust gas. Both of them are always operated without time-sharing.

The whole constructions of laminated layer of the gas composition sensors of FIG. 13(c) to (m) are basically constructed by combination of the heater A, the sensing elements B, D and the reference element C of FIG. 13(a) and (b). Some are constructed in such that the two sensing elements B (D) or the two reference element C are formed in a unit, and others are constructed in such that the two sensing elements B (D) or the two reference element C are arranged in an integrated element.

Figure 14:
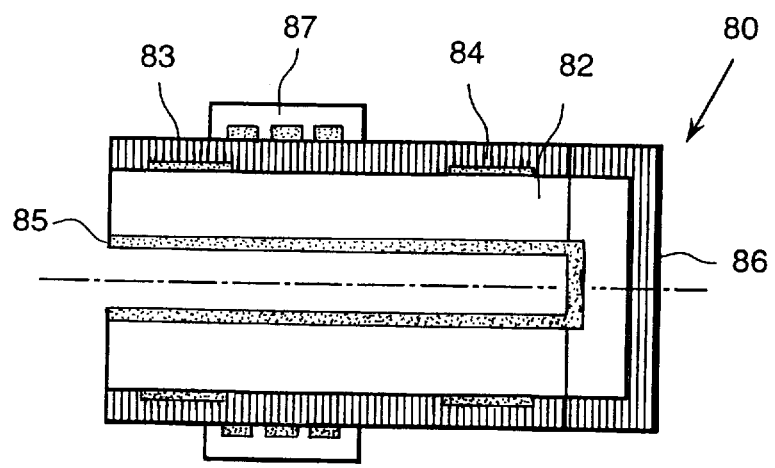
FIG. 14 is a cross-sectional view showing a further embodiment of a cylindrical gas composition sensor in accordance with the present invention.

A further embodiment of a gas composition sensor in accordance with the present invention may be constructed as shown in FIG. 14. The gas composition sensor 80 basically has a cylindrical body with a closed front end of a solid electrolyte body 82 as the same as that of the gas composition sensor 1 of FIG. 1. A reference electrode 85 exposed to atmosphere is arranged inside the cylinder of the solid electrolyte body 82, and a detecting electrode in the low temperature side 84 and a detecting electrode in the high temperature side 83 exposed to an exhaust gas are arranged in the top front outer portion of the cylinder of the solid electrolyte body 82. A member 86 covers the cylindrical portion of the solid electrolyte body 85. The member 86 is for limiting diffusion of gas and formed of a porous film to cover the whole of the detecting electrodes 83, 84. A heater 87 is arranged in the periphery of the diffusion limiting member 86.

It can be understood from the above description that the gas composition sensor in accordance with the present invention is usable since it is easily to be mounted, low in cost, small in size and light in weight by constructing the pair of sensing elements and the heater in a unit. Further, the gas composition sensor can selectively detect specified gas components. Accordingly, the gas composition sensor can diagnose catalyst for an engine with high accuracy, and can detect an exhaust gas recirculation ratio of an engine intake system and an air-to-fuel ratio at purging fuel vapor. Thus, it is possible to perform a total control of the intake system and the exhaust system of the engine. Further, the gas composition sensor can be also used as a detector for detecting leakage of various kinds of fuel gases.

What is claimed is:

1. A gas composition sensor for detecting oxygen, hydrocarbon-group fuel, or a combusted composition, comprising a pair of sensing elements, each having a zirconia solid electrolyte body, a concentration cell composed of a platinoid metal catalytic detecting electrode and a reference electrode opposite to each other, and a gas diffusion limiting member coating said detecting electrode, a heater for setting, in substantially the same time phase, both of said sensing elements to operating temperatures different from each other for said sensing elements to have sensitivity coefficients to specified gas components different from each other, said sensing elements being operatively arranged and operable to selectively detect a specified gas component by way of said sensing elements having the different sensitivity coefficients.

2. A gas composition sensor according to claim 1, wherein said pair of sensing elements are arranged to share at least one of said solid electrolyte body, said reference electrode and said heater.

3. A gas composition sensor according to claim 1, wherein said heater for heating said pair of sensing elements has an electric insulator member laterally of said sensing elements and a heat insulating member laterally of detected gas and reference gas flow passages.

4. A gas composition sensor according to claim 1, wherein said pair of sensing elements share said solid electrolyte body, and share any one of said reference electrode and said diffusion limiting member.

5. A gas composition sensor according to claim 1, wherein said pair of sensing elements share said diffusion limiting member, and share at least one of said solid electrolyte body, said reference electrode and said heater.

6. A gas composition sensor according to claim 1, wherein said pair of sensing elements comprise high and low temperature portions such that an operating temperature T1 of said sensing element in the low temperature position is not higher than 450° C. and the difference between an operating temperature Th of said sensing element in the high temperature portion and the operating temperature T1 is not lower than 100° C.

7. A gas composition sensor according to claim 1, which further comprises a controller for sequentially controlling said pair of sensing elements using a micro-computer.

8. A gas composition sensor according to claim 7, wherein said controller is operatively arranged to control a temperature of one of said sensing elements in the low temperature so as to be stabilized within a predetermined time period after starting operation, the other of said sensing elements in the high temperature portion being positioned so that a temperature thereof is controlled to a target temperature as said one sensing element in the low temperature portion is controlled, thereby selectively detecting hydrocarbon.

9. A gas composition sensor according to claim 7, wherein said controller is operatively arranged to introduce a reference air into the surrounding of said sensing elements, a characteristic changing rate in an output function of said gas composition sensor being calibrated by comparing an output value under an oxygen concentration of the introduced reference air with a stored initial output value.

10. A gas composition sensor for detecting at least one of oxygen and any one of hydrocarbon-group fuel and a combusted composition, comprising a pair of sensing elements, each having a zirconia solid electrolyte body, a concentration cell composed of a platinoid metal catalytic detecting electrode and a reference electrode opposite to each other, and a gas diffusion limiting member coating said detecting electrode, wherein said detecting electrode is arranged so as to be exposed to the at least one of oxygen and any one of the hydrocarbon-group fuel and the combusted composition to be detected, and said reference electrode is exposed to any one of atmospheric air and an atmosphere containing oxygen, and said gas composition sensor further comprises a heater for heating said pair of sensing elements, said heater being coated with a ceramic layer to be heat-insulated and arranged so as to heat said pair of sensing elements to different temperatures in substantially the same time phase.

11. A gas composition sensor for detecting at least one of oxygen and any one of hydrocarbon-group fuel and combusted composition, comprising a pair of sensing elements, each having a zirconia solid electrolyte body, a concentration cell composed of a platinoid metal catalytic detecting electrode and a reference electrode opposite to each other, and a gas diffusion limiting member coating said detecting electrode, wherein said detecting electrode is arranged so as to be exposed to the at least one of oxygen and any one of the hydrocarbon-group fuel and the combusted composition to be detected, and said reference electrode is exposed to any one of atmospheric air and an atmosphere containing oxygen, and said gas composition sensor further comprises a heater for heating said pair of sensing elements to temperatures different from each other in substantially the same time phase, an insulating ceramic layer being provided between said heater and said sensing elements to moderate strain due to thermal expansion difference, a ceramic heat insulating coating layer being selectively provided in said heater in a portion opposite to said sensing elements.

12. A gas composition sensor for detecting oxygen and any one of hydrocarbon group fuel and combustible composition produced after combustion, comprising a pair of cylindrically shaped sensing elements, each having a zirconia solid electrolyte body, a concentration cell composed of a platinoid metal catalytic detecting electrode and a reference electrode opposite to each other, and a gas diffusion limiting member coating said detecting electrode, wherein said reference electrode is arranged over an entire inside surface of said solid electrolyte body and an outside surface of said detecting electrodes in the pair of said sensing elements is coated with a porous ceramic layer comprising said gas diffusion limiting member.

13. A gas composition sensor according to claim 12, wherein said detecting electrode is arranged so as to be exposed to the oxygen and any one of the hydrocarbon group fuel and the combustible composition produced after combustion to be detected, and said reference electrode is exposed to any one of atmospheric air and an atmosphere containing oxygen, and said gas composition sensor further comprises a heater for heating said pair of sensing elements being mounted on a porous ceramic layer near a portion of said detecting electrode, a porous ceramic heat insulating coating layer being provided in said heater in the portion opposite to said detecting electrode.

14. A gas composition sensor for detecting at least one of oxygen and any one of hydrocarbon-group fuel and combusted composition, comprising:

a zirconia solid electrolyte body;

a pair of sensing elements, one of which sensing elements is a first concentration cell having a first platinoid metal catalytic detecting electrode and a reference electrode, arranged opposite each other to sandwich said zirconia solid electrolyte therebetween, and a second concentration cell having a second platinoid metal catalytic detecting electrode and said reference electrode opposite each other to sandwich said zirconia solid electrolyte therebetween;

a gas diffusion limiting member in the form of a coating on said detecting electrodes;

a heater for heating said pair of sensing elements;

wherein said pair of sensing elements have a positional relationship with said heater to be heated in substantially the same time phase to different operating temperatures specific to gas components so as to have sensitivity coefficients specific to respective specific gas components.

15. A gas composition sensor according to claim 14, wherein density and thickness of said diffusion limiting member are sized to limit diffusion of gas to said detecting electrodes.

16. A gas composition sensor according to claim 15, wherein said diffusion limiting member exceeds 50 $\mu$m in thickness.

* * * * *